US009801377B2

(12) United States Patent
Liu et al.

(10) Patent No.: US 9,801,377 B2
(45) Date of Patent: Oct. 31, 2017

(54) FORMULATIONS OF CLOMAZONE

(71) Applicant: FMC Corporation, Philadelphia, PA (US)

(72) Inventors: Hong Liu, Pennington, NJ (US); Michael R. Welch, Cliffwood Beach, NJ (US); Paul Nicholson, Ewing, NJ (US); Jeffrey A. Cook, Lawrenceville, NJ (US); Catherine Ranin, Burlington, NJ (US); Sandra L. Shinn, Columbus, NJ (US); Robert F. Pepper, Bordentown, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 13/920,788

(22) Filed: Jun. 18, 2013

(65) Prior Publication Data

US 2014/0031231 A1 Jan. 30, 2014

Related U.S. Application Data

(60) Provisional application No. 61/676,588, filed on Jul. 27, 2012, provisional application No. 61/681,693, filed on Aug. 10, 2012, provisional application No. 61/683,465, filed on Aug. 15, 2012.

(51) Int. Cl.
*A01N 43/80* (2006.01)
*A01N 25/28* (2006.01)
*A01N 33/18* (2006.01)
*A01N 33/22* (2006.01)
*A01N 39/02* (2006.01)
*A01N 43/56* (2006.01)

(52) U.S. Cl.
CPC ............ *A01N 43/80* (2013.01); *A01N 25/28* (2013.01); *A01N 33/18* (2013.01); *A01N 33/22* (2013.01); *A01N 39/02* (2013.01); *A01N 43/56* (2013.01)

(58) Field of Classification Search
None
See application file for complete search history.

(56) References Cited

U.S. PATENT DOCUMENTS

| | | | |
|---|---|---|---|
| 3,429,827 A | 2/1969 | Henn | |
| 3,577,515 A | 5/1971 | Vandergaer | |
| 4,046,741 A | 9/1977 | Scher | |
| 4,107,292 A | 8/1978 | Nemeth | |
| 4,140,516 A | 2/1979 | Scher | |
| 4,280,833 A | 7/1981 | Beestman | |
| 4,285,720 A | 8/1981 | Scher | |
| 4,360,376 A | 11/1982 | Koestler | |
| 4,405,357 A | 9/1983 | Chang | |
| 4,417,916 A | 11/1983 | Beestman | |
| 4,448,929 A | 5/1984 | Rodson | |
| 4,497,793 A | 2/1985 | Simkin | |
| 4,563,212 A | 1/1986 | Becher | |
| 4,643,764 A | 2/1987 | Scher | |
| 4,853,223 A | 8/1989 | Graf | |
| 4,889,719 A | 12/1989 | Ohtsubo | |
| 4,936,901 A † | 6/1990 | Surgant, Sr. et al. | |
| 4,938,797 A | 7/1990 | Hasslin | |
| 4,956,129 A | 9/1990 | Scher | |
| 5,006,161 A | 4/1991 | Hasslin | |
| 5,098,468 A | 3/1992 | Puritch | |
| 5,290,751 A | 3/1994 | Fiard | |
| 5,332,584 A | 7/1994 | Scher | |
| 5,354,742 A † | 10/1994 | Deming | |
| 5,583,090 A | 12/1996 | Stern | |
| 5,597,780 A | 1/1997 | Lee et al. | |
| 5,643,591 A | 7/1997 | Mehra | |
| 5,783,520 A † | 7/1998 | Anderson | |
| 5,925,464 A | 7/1999 | Mulqueen et al. | |
| 6,218,339 B1 * | 4/2001 | Becker | A01N 43/80 504/140 |
| 6,358,520 B1 | 3/2002 | Lo et al. | |
| 6,380,133 B2 | 4/2002 | Becker et al. | |
| 6,419,942 B1 | 7/2002 | Lo et al. | |
| 6,440,902 B1 † | 8/2002 | Szamosi | |
| 6,555,122 B2 | 4/2003 | Lo et al. | |
| 6,797,277 B2 | 9/2004 | Heier et al. | |
| RE38,675 E † | 12/2004 | Lee | |
| 7,754,655 B2 * | 7/2010 | Wolf | A01N 25/28 264/4.1 |

(Continued)

FOREIGN PATENT DOCUMENTS

EP 17409 10/1980
EP 551796 7/1993

(Continued)

OTHER PUBLICATIONS

R V. Dargar et al. "Clomazone Measurement by Enzyme-Linked Immunosorbent Assay" Journal of Agricultural Food Chemistry, 1991, 39, pp. 813-819
S. J. Halstead et al. "Effect of Rate and Carrier on Clomazone Movement Off-site", Weed Technology,vol. 2, No. 2, Apr. 1988, pp. 179-182.
Mervosh et al., Weed Science, 1995, 43(3), p. 445-453.
Locke et al., Chemosphere, 1996, 33(7), p. 1213-1225.
Dargar et al., J. Agric. Food Chem., 1991, 39(4), p. 813-819.
Mills et al., Weed Science, 1989, 37(2), p. 217-222.
Mervosh et al., J. Agric. Food Chem., 1995, 43(2), p. 537-543.
Food and Agricultural Industries 1/95, 1995, Environmental Protection Agency, Chapter 9.2.2 Pesticide Application.
Dragan et al., "Microencapsulated Organophosphorous Insecticides", Research Article 1987, vol. 4(2), pp. 97-105; Abstract Only.
Memorandum of the United States Environmental Protection Agency Mar. 15, 1988.
Turner et al., "Volatilization of Microencapsulated and Conventionally Applied Chlorpropham in the Field", Agronomy Journal, vol. 70, p. 933-939.

(Continued)

*Primary Examiner* — John Pak
*Assistant Examiner* — Daniel Branson
(74) *Attorney, Agent, or Firm* — FMC Corporation

(57) ABSTRACT

New formulations of clomazone are provided, as well as new methods for making formulations of clomazone. The new formulations provide improved efficacy, decreased volatility, and/or increased loading of clomazone over the clomazone formulations in the prior art.

15 Claims, No Drawings

(56) References Cited

U.S. PATENT DOCUMENTS

| | | |
|---|---|---|
| 2004/0077449 A1 | 4/2004 | Biermann et al. |
| 2009/0099024 A1 | 4/2009 | Casana Giner et al. |
| 2009/0226496 A1 † | 9/2009 | Mulqueen |
| 2010/0234225 A1 | 9/2010 | Dexter et al. |
| 2010/0248963 A1 | 9/2010 | Becher et al. |
| 2012/0028800 A1 | 2/2012 | Mathews et al. |
| 2012/0142533 A1 | 6/2012 | Richard et al. |
| 2014/0200141 A1* | 7/2014 | Shroff .................. A01N 25/04 504/138 |

FOREIGN PATENT DOCUMENTS

| | | |
|---|---|---|
| EP | 1562433 | 8/2005 |
| EP | 1 840 145 A1 | 10/2007 |
| FR | 2591857 | 5/2003 |
| GB | 1371179 | 10/1974 |
| NO | 97/01274 A1 | 1/1997 |
| NO | 00/54590 A1 | 9/2000 |
| NO | 2005/015999 A1 | 2/2005 |
| WO | WO 90/08468 | 9/1990 |
| WO | WO 94/13139 | 6/1994 |
| WO | WO 95/13698 | 5/1995 |
| WO | 96/14743 A1 | 5/1996 |
| WO | WO 96/22159 A1 † | 7/1996 |
| WO | 96/39822 A1 | 12/1996 |
| WO | WO 96/39822 A1 † | 12/1996 |
| WO | 98/24317 A1 | 6/1998 |
| WO | 00/10392 A1 | 3/2000 |
| WO | 2007101019 A2 | 9/2007 |
| WO | 2009/135492 A1 | 11/2009 |
| WO | 2010/093970 A2 | 8/2010 |
| WO | 2011107015 A1 | 9/2011 |
| WO | 2011113052 A2 | 9/2011 |
| WO | 2011121407 A1 | 10/2011 |
| WO | WO 2011/121407 A1 † | 10/2011 |
| WO | 2012/024524 A1 | 2/2012 |
| WO | 2012/071248 A1 | 5/2012 |

OTHER PUBLICATIONS

Halstead et al., "Proceedings, North Central Weed Control Conference, Dec. 10-12, 1985, vol. 40, factors affecting the off-site movement of FMC-57020".

Halstead, "Factors affecting the off-site movement of Clomazone", thesis submitted to University of Wisconsin, Madison, 1987.

"Manual on Development and Use of FAO and WHO Specifications for Pesticides"; First Edition 2002. .

Keifer, David W. et al., "Microencapsulated clomazone: formulation stability, tank mix volatility, and solvent effects", Database Caplus (Online), Chemical Abstracts Service, Columbus, Ohio, US; abstract, 2007.

* cited by examiner
† cited by third party

FORMULATIONS OF CLOMAZONE

CROSS REFERENCE TO RELATED APPLICATIONS

This application claims priority to, U.S. Provisional Patent Application Ser. No. 61/676,588 filed Aug. Jul. 27, 2012, U.S. Provisional Patent Application Ser. No. 61/681,693 filed Aug. 10, 2012, and U.S. Provisional Patent Application Ser. No. 61/683,465 filed Aug. 15, 2012, the contents of which are hereby incorporated herein in their entirety.

FIELD OF THE DISCLOSED SUBJECT MATTER

The present invention relates to the field of agrochemical compositions and formulations.

DESCRIPTION OF RELATED ART

Clomazone, the common name for 2-(2-chlorophenyl) methyl-4,4-dimethyl-3-isoxazolidinone, is an active ingredient in highly effective herbicides that are selective against perennial weeds, including grasses and broadleaves. Clomazone works by inhibiting the biosynthesis of carotenoids in the plant; a plant affected by clomazone exhibits progressive whitening with increased dosage.

Herbicides containing clomazone are applied to the soil for control of weeds on beans, cabbage, cucumbers, cotton, melons, mint, peas, peppers, rice, soybeans, squash, sugarcane, sweet potatoes, tobacco and tuberous vegetables. Such herbicides are selective against perennial weeds, including grasses and broadleaves.

Clomazone is considered to be highly volatile. When it is applied to soil in a target area, under certain conditions clomazone may migrate or diffuse to adjacent areas causing whitening or bleaching of beneficial plants near treated fields. While this whitening and bleaching on non-targeted plants, indicative of the mode of action of clomazone, may be temporary when plants are exposed to sufficiently low concentrations, it is unwelcome, even when it does not result in the destruction of the plant. Accordingly, the label for the use of clomazone-containing herbicides, such as Command® (in the US, FMC Corporation) and Centium® (in Europe, FMC Corporation), lists a number of restrictions on how the herbicide is to be used, including weather conditions, spray volume and pressure, droplet size, and distance from areas where plants are in commercial production. For example, for preemergent applications, clomazone-containing herbicide is not to be applied within 1,500 feet (500 meters) of commercial fruit, nut, or vegetable production or commercial greenhouses or nurseries.

Microencapsulated formulations of clomazone have been developed to address the problem of clomazone volatility. Various methods of microencapsulating clomazone are disclosed in U.S. Pat. Nos. 5,583,090; 5,597,780; 5,783,520; 6,380,133; 6,440,902; RE38,675; and U.S. Patent Publication No. 2010/0234225. U.S. Pat. No. 5,597,780 to Lee et al., for example, addresses the high volatility of clomazone by teaching a low volatility formulation of clomazone where the clomazone is microencapsulated in a shell of polyurea. Microencapsulated forms of clomazone have been commercialized and are sold globally, including in the United States where one formulation is marketed under the name Command® 3ME (FMC Corporation).

However, existing microencapsulated formulations of clomazone are limited in the clomazone concentration they can achieve, and in the ability to create formulations in which other active ingredients are microencapsulated with the clomazone. The present invention improves on existing microencapsulated formulations of clomazone by providing a formulation that can achieve a heretofore unobtainable concentration of clomazone in the microcapsule.

It is sometimes useful to use a second or third agricultural agent along with clomazone to broaden the spectrum of activity. In order to maintain volatility control over both ingredients, formulations of clomazone and a second active ingredient within the microcapsule have been described in U.S. Pat. No. 6,440,902 to Szamosi. However, some agricultural agents are incompatible with clomazone and have not yet been able to be co-encapsulated with clomazone. Thus, formulations including clomazone and a second active agent that is incompatible with clomazone remain to be addressed. The present invention improves on the prior art by providing a formulation that allows the heretofore unachievable coexistence of clomazone with sulfentrazone in the microcapsule.

In addition, capsule suspension formulations in which clomazone microcapsules are combined with other agricultural agents are often chemically or physically unstable. Moreover, a significant portion of the weight of commercially available suspensions of clomazone microcapsules is due to inactive ingredients. The high level of inert ingredients present in commercially available herbicides adds to the volume and weight of the herbicides, resulting in additional production costs, packaging costs, transportation costs, storage costs, handling costs, and other costs associated with making, transporting, storing, and using the herbicide. Additional drawbacks to liquid formulations include the difficulty of maintaining the stability of the formulations when stored in cold or hot climates. Another problem with the use of clomazone either as an aqueous solution, such as Command® 4EC, or as an aqueous suspension of microencapsulated clomazone, such as Command® 3ME, is the difficulty associated with accidental spills. Accidental release countermeasures include the use of dikes to confine the spill, use of absorbents, and neutralization of the area by a solution of potassium hydroxide in methanol. Cleaning up a spill of a liquid generates lots of waste material.

In light of these concerns, it would be advantageous to have a lightweight dry granular formulation of clomazone to which at least one other agriculturally active agent can be added that is physically and chemically stable and exhibits volatility control of clomazone.

One example of a process for production of solid water-dispersible compositions of microencapsulated pesticides is described in U.S. Pat. No. 5,354,742 to Deming et al. In that process, typical spray-drying adjuvants are then added to such an aqueous suspension of microcapsules, and the resulting suspension is spray-dried as described therein to produce water-dispersible granules containing the microcapsules. The spray-drying adjuvants (also referred to as "suspension adjuvants", "agglomeration adjuvants" and "formulation adjuvants") are preferably water-soluble salts such as ammonium sulfate or sodium, potassium or calcium chlorides. The adjuvants may also include surfactants, water-soluble polymers, higher alcohols and other water-soluble or water-dispersible components such as gums, clays and silicas. However, no ranges are given in the patent for the amount or amounts of such adjuvants utilized in the process. Among the additional adjuvants are included water-soluble polymers such as polyvinyl pyrrolidone (PVP) and polyvinyl alcohol (PVA) electrolytes. The only example in which any such material is used is Example 8 in which the microcapsule suspension contains 0.49% by weight PVP. According to the patent the formulation adjuvants function to cause agglomeration of microcapsules during the spray-drying. As water is removed from each droplet emanating from the spray nozzle, an aggregate is formed containing many small microcapsules associated together with a fine layer of adjuvant homogenously interspersed between each microcapsule. The adjuvant thus functions both by separating the microcapsules from each other and by bridging the capsules to each other, thus producing agglomeration of the capsules into larger granules which are dispersible in water. Problematically, techniques of this type are not suitable for producing water-dispersible granules or agglomerated compositions of pesticidal microcapsules having relatively small particle size and relatively thin walls. Attempts to produce dispersible materials from such microcapsules using the technique of U.S. Pat. No. 5,354,742 resulted in a sticky material which could not be dispersed in water. Additionally, all of the examples and teachings of U.S. Pat. No. 5,354,742 are directed to microcapsules with cores that comprise pure pesticides. Furthermore, no efficacy or volatility data for the formulations was presented. Because of the difficulties in forming microcapsules with cores that comprise pure clomazone, other methods of developing a dry clomazone-based herbicide are needed.

The shortcomings of U.S. Pat. No. 5,354,742 are addressed in part in U.S. Pat. Nos. 6,358,520; 6,555,122; and 6,419,942. In that series of related patents solid water-dispersible compositions containing microencapsulated pesticides are produced by spray-drying an aqueous suspension of said pesticides in the presence of a water-soluble polymer, preferably polyvinyl alcohol. All of the examples and teachings of those patents are directed to pesticides where the active ingredient comprises 42 to 48% by weight of the total formulation. No guidance on how to select the appropriate levels of components was presented, and data on the volatility of the formulations was presented. It would be advantageous to provide solid water-dispersible compositions containing microencapsulated pesticides with higher active ingredient concentrations, improved water dispersibility, and an improved ability to work with smaller, superior microcapsules.

SUMMARY OF THE DISCLOSED SUBJECT MATTER

The present invention provides methods and materials for making compositions containing encapsulated clomazone with improved efficacy and stability, decreased volatility compared to commercially available encapsulated formulations of clomazone, and/or increased loading levels.

In one embodiment, the present invention comprises a controlled-volatility formulation of clomazone. In aspects of this embodiment, the formulation has clomazone volatility control of at least 75%, at least 80%, at least 90%, or at least 94%.

In another aspect of this embodiment, the controlled volatility formulation comprises multilayered particles. The core of the particle contains clomazone. The first encapsulating layer of the particle contains a water-insoluble polymer. And the second encapsulating layer contains a water-soluble polymer. In further aspects, the core is either a solid composition containing clomazone or a liquid composition containing clomazone.

In another aspect of this embodiment, the clomazone comprises at least 50% by weight of the particle. In a further aspect, the weight ratio of the water-soluble polymer to clomazone is from about 1:6 to about 1:4.

In another aspect of this embodiment, the water-insoluble polymer is polyurea.

In another aspect of this embodiment, the water-soluble polymer is polyvinyl alcohol.

In another aspect of this embodiment, a solid herbicidal composition is provided which contains the multilayered particles. In a further aspect, the second encapsulating layer contains a salt as well as the water-insoluble polymer. In a yet further aspect, the salt may be one or more of: alkali metal halide, alkaline earth metal halide, ammonium halide, alkali metal sulfate, alkaline earth metal sulfate, ammonium sulfate, alkali metal nitrate, alkaline earth metal nitrate, ammonium nitrate, alkali metal carbonate, and ammonium carbonate. In a further aspect, the weight ratio of the first encapsulating layer to the second encapsulating layer is in from about 3:1 to 1:3, or from about 1.5:1 to 1:1.5.

In another aspect of this embodiment, the composition has clomazone volatility control of at least 80%. In a further aspect, the composition has clomazone volatility control of at least 90%.

In another aspect of this embodiment, the multilayered particles are prepared by first preparing an aqueous suspension of particles comprising the clomazone-containing core and the first encapsulating layer, next adding a water-soluble polymer to the aqueous suspension, and finally spray drying the resulting mixture. The multilayered particles produced contain at least 50% by weight of clomazone. In a further aspect, the weight ratio of water-soluble polymer to clomazone is from about 1:6 to about 1:4. In other, further aspects, the multilayered particles contain clomazone in an amount from about 50% by weight to about 80% by weight, or about 55% by weight to about 70% by weight. In yet further aspects, the weight ratio of the first layer to the polyvinyl alcohol is from about 3:1 to 1:3, or about 1.5:1 to 1:1.5.

In another aspect of the present embodiment, a method of controlling weeds is provided in which an herbicidally effective amount of the multilayered particles is applied to an area where weeds are present. In a further aspect, the weeds present may be one or more of barnyard grass, broadleaf signalgrass, crabgrass, foxtail, goosegrass, *panicum*, Johnsongrass, cupgrass, field sandbur, Bermuda grass, red rice, itch grass, velvetleaf, spurred anoda, common ragweed, Jimsonweed, lambsquarter, Pennsylvania smartweed, prickly *sida*, purslane, redweed, Venice mallow, cocklebur, dayflower, Florida beggarweed, Florida pusley, Kochia, redvine, tropic *croton*, wild poinsettia, balloonvine, black nightshade, curly dock, joint vetch, shattercane, and morning glory.

In another embodiment, the present invention comprises a mixture of clomazone and linseed oil. In an aspect of this embodiment, the clomazone is at least partially dissolved in the linseed oil. In further aspects, the mixture contains about 80 to about 97 weight percent of clomazone, about 85 to about 90 weight percent clomazone, about 90 to about 95 weight percent clomazone, and about 95 to about 97 weight percent clomazone. In a yet further aspect, the mixture is either a suspension or a solution.

In another aspect of the current embodiment, the mixture is part of a microcapsule, which comprises the mixture and a polymer shell. In a further aspect, the polymer shell comprises polyurea. In a further aspect, the mixture contains about 80 to about 97 weight percent of clomazone.

Another aspect of the current embodiment is an herbicidal composition comprising a plurality of the clomazone-containing microcapsules. In a further aspect, microcapsules are suspended in an aqueous solution. In a yet further aspect, the aqueous solution further comprises ammonium sulfate.

Another aspect of the current embodiment is a microcapsule comprising a polyurea shell encapsulating a material comprising clomazone and linseed oil. In further aspects, the microcapsule contains about 80 to about 97 weight percent of clomazone, about 85 to about 90 weight percent clomazone, about 90 to about 95 weight percent clomazone, and about 95 to about 97 weight percent clomazone.

Another aspect of the current embodiment is an herbicidal composition comprising a plurality of microcapsules containing clomazone and linseed oil. In a further aspect, the microcapsules are suspended in an aqueous solution. In a yet further aspect, the aqueous liquid further comprises ammonium sulfate.

Another aspect of the current embodiment is a method of controlling weeds whereby an herbicidally effective amount of an herbicidal composition containing polyurea microcapsules of clomazone is applied to an area where weeds are present. In a further aspect, the weeds present include one or more of the following: barnyard grass, broadleaf signalgrass, crabgrass, foxtail, goosegrass, *panicum*, Johnsongrass, cupgrass, field sandbar, Bermuda grass, red rice, itch grass, velvetleaf, spurred anoda, common ragweed, Jimsonweed, lambsquarter, Pennsylvania smartweed, prickly *sida*, purslane, redweed, Venice mallow, cocklebur, dayflower, Florida beggarweed, Florida pusley, Kochia, redvine, tropic *croton*, wild poinsettia, balloonvine, black nightshade, curly dock, joint vetch, shattercane, and morning glory.

In another embodiment, the present invention provides methods for making water-dispersible granules for delivering agricultural chemicals to a crop. These methods involve forming a water-dispersible powder containing an agriculturally active agent, milling the powder, and combining the powder with an aqueous solution of microencapsulated clomazone to form water-dispersible granules.

In one aspect of this embodiment, the granules are formed by kneading the aqueous solution of microencapsulated clomazone into the milled water-dispersible powder, then subjecting the resulting wetted powder to pan pelletization and drying the resulting granules. The granules themselves represent a further aspect of this embodiment.

In another aspect of this embodiment, the granules are formed by kneading water into the milled water-dispersible powder, extruding the resulting dough into granules, spray-coating the granules with the aqueous solution of microencapsulated clomazone, and drying the granules. The granules themselves represent a further aspect of this embodiment.

In another aspect of this embodiment, the milled water-dispersible powder is mixed with the aqueous solution of microencapsulated clomazone, then spray-dried to form granules. The granules themselves represent a further aspect of this embodiment.

In a further aspect of this embodiment, the agriculturally active agent is an herbicide. In a further aspect, the herbicide is selected from the group consisting of aclonifen, napropamide, and a combination thereof. In a further aspect, the water-dispersible powder may contain one or more of a wetting agent, a dispersant, a defoamer and a carrier.

In another embodiment of the present invention, a composition is provided that coencapsulates clomazone with other agriculturally active ingredients while maintaining volatility control. In one aspect of this embodiment, the composition exhibits volatility control of at least 75%, preferably at least 80%, 90%, or 95%.

In another aspect of this embodiment, the composition comprises clomazone, metolachlor, and sulfentrazone encapsulated in a microcapsule. In further aspects of this embodiment, the clomazone, metolachlor, and sulfentrazone taken together make up at least 40% by weight of the composition. In another aspect, the clomazone makes up at least 10% by weight of the composition. In another aspect, the metolachlor makes up at least 10% by weight of the composition. In another aspect, the sulfentrazone makes up at least 10% by weight of the composition. In another aspect, the volatility control of the clomazone, metolachlor, and sulfentrazone composition is at least 75%, preferably at least 80%, more preferably at least 90%, even more preferably at least 95%. In another aspect, the volatility control of the clomazone, metolachlor, and sulfentrazone composition after three months storage at 50° C. is at least 75%, preferably at least 80%, more preferably at least 90%, even more preferably at least 95%.

In another aspect of this embodiment, the composition comprises clomazone and metazachlor encapsulated in a microcapsule. In a further aspect of this embodiment, napropamide is co-encapsulated with the clomazone and metazachlor. In another aspect, the volatility control of the clomazone and metazachlor composition is at least 75%, preferably at least 80%, more preferably at least 90%, even more preferably at least 95%. In another aspect, the volatility control of the clomazone and metazachlor composition after three months storage at 50° C. is at least 75%, preferably at least 80%, more preferably at least 90%, even more preferably at least 95%.

In another aspect of this embodiment, the composition comprises clomazone and pendimethalin encapsulated in a microcapsule. In another aspect, the volatility control of the clomazone and pendimethalin composition is at least 75%, preferably at least 80%, more preferably at least 90%, even more preferably at least 95%. In another aspect, the volatility control of the clomazone and pendimethalin composition after three months storage at 50° C. is at least 75%, preferably at least 80%, more preferably at least 90%, even more preferably at least 95%.

DETAILED DESCRIPTION OF EXEMPLARY EMBODIMENTS

Microcapsules of Clomazone

In accordance with one embodiment of the invention, a formulation of clomazone is provided. The formulation comprises microcapsules of clomazone wherein the microcapsules contain a high-concentration solution of clomazone and linseed oil.

Another aspect of the present embodiment is a method of preparing an herbicidal composition. This method combines water and a polymeric dispersant to which a solution comprising clomazone, linseed oil, and polyisocyanate are added. The prepared mixture is then emulsified, and polyfunctional amines are added to produce a plurality of microcapsules containing clomazone and linseed oil. In a further aspect, the method yields a high loading level of clomazone in the herbicidal composition by adding ammonium sulfate, xanthan gum or a mixture thereof in powdered form.

Another aspect of the present embodiment is a method of using an herbicidal composition that includes a dispersion of the clomazone-containing microcapsules.

One of the purposes of the present embodiment is to provide for a clomazone-containing herbicide that contains a higher loading level of clomazone, while at the same time improving or maintaining the herbicidal activity of the herbicide.

Another purpose of the present embodiment is to provide for a clomazone-containing herbicide that contains a higher loading level of clomazone, while at the same time reducing or maintaining the volatility of the clomazone, so that the problem of off-site injury is reduced.

To increase the amount of clomazone in microencapsulated clomazone-containing herbicides, several methods can be employed, including increasing the concentration of clomazone in the microcapsules, and increasing the loading level of microcapsules in the aqueous herbicidal mixture. According to the present embodiment, the increase of concentration of clomazone in the encapsulated material is achieved by a specific selection of materials used during the microencapsulation process, and by specific selection of reaction conditions, as described fully below. According to another aspect of the present embodiment, to increase the amount of microcapsules in the aqueous herbicidal mixture, specific selection of materials and preparative steps are used to generate the aqueous portion of the herbicidal mixture, as described fully below.

Increasing the loading level of clomazone in the microcapsules will effectively increase the over-all loading level of clomazone in the clomazone-containing herbicide, which in turn leads to lowering costs related to manufacturing, packaging, handling, transporting, storing, and using of the herbicide. One of the embodiments of the present invention is a microcapsule encapsulating a solution of linseed oil and clomazone wherein the clomazone is 85 to 97 weight percent of the encapsulated material. This loading level of clomazone is greater than in the previously disclosed or commercially available microencapsulated clomazone.

Increasing the loading level of the microcapsules in the herbicide increases the loading level of clomazone compared to the total volume of the herbicide, leading to lowering costs related to manufacturing, packaging, handling, transporting, storing, and using of the herbicide. Another embodiment of the present invention is the omission of the addition of water after the formation and annealing of the formed microcapsules, while at the same time adding components of the composition without sacrificing the characteristics of the herbicide such as stability and ability to mix with other herbicides.

In these processes an aqueous suspension of microcapsules comprising a polyurea shell surrounding a core comprising clomazone dissolved in an inert organic solvent is prepared by (i) creating an aqueous solution by combining water and a polymeric dispersant; (ii) adding an organic solution comprising clomazone, the inert organic solvent, and polyisocyanate, to generate a mixture; (iii) emulsifying the mixture; and (iv) adding a polyfunctional amine. As described, the organic solution comprises an organic solvent, clomazone, and polyisocyanate. The organic solution may further comprise adjuvants, such as surfactants. As described, the aqueous solution comprises water and a polymeric dispersant. The aqueous solution may further comprise adjuvants, which can for example aid in formation of the microcapsules. The herbicidal composition thus prepared comprises at least 50 weight percent clomazone. In one aspect of the present embodiment the herbicidal composition comprises between 50 and 97 weight percent clomazone. In one preferred aspect the herbicidal composition comprises between 55 and 65 weight percent clomazone.

The four preparative steps (i), (ii), (iii), and (iv) should preferably be performed sequentially. However, such steps are not all-encompassing. Additional steps to generate a clomazone-containing herbicide may be required. There may be preparative steps prior to step (i), there may be intermediate steps between any of these four steps, and there may be preparative steps necessary after step (iv). For example, to obtain a commercially preferred herbicide, it may be necessary to adjust the characteristics of the continuous aqueous phase of the herbicidal composition obtained by the process defined by steps (i) through (iv), by adding excipients that adjust the pH, viscosity, shelf stability, density, and other physical or chemical properties.

The term "clomazone" as used in the above processes means a composition comprising at least 90% by weight pure 2-(2-chlorophenyl) methyl-4,4-dimethyl-3-isoxazolinone. In one embodiment the clomazone may be technical grade clomazone with purity range of 90 to 95% by weight. In another embodiment, the clomazone may be a composition comprising more than 95% by weight pure 2-(2-chlorophenyl) methyl-4,4-dimethyl-3-isoxazolinone. The clomazone as used as an ingredient in Formulations A through H below comprised 94.8% to 96.8% by weight pure clomazone. The term "pure clomazone" means 100% pure 2-(2-chlorophenyl) methyl-4,4-dimethyl-3-isoxazolinone. The calculated composition values in the analytical portion of the description of each Formulation adjust for purity levels of the clomazone in the organic composition corresponding to organic composition of step (b) in the above method. However, higher purity grade clomazone reagents may be used to yield higher loading levels of clomazone in microcapsules, and ultimately in the herbicide.

In the preparative step (i) of the above method of preparing an aqueous suspension of microcapsules, water is combined with a polymeric dispersant. In a preferred aspect of this embodiment, the polymeric dispersant is well mixed in water to generate an aqueous solution of the dispersant. The polymeric dispersant can be present in an amount of from 0.5% by weight to 10% by weight of all components in the total composition, preferably in an amount of from 0.8% by weight to 1.5% by weight of all components in the total composition. In one aspect of the present embodiment, the polymeric dispersant is lignin. Lignin is a complex natural polymer found in wood. Examples of lignin include AHR 2438B, Betz 402, Borresperse N, Borresperse NA, D 419-6, Diwatex 30FKP, Flowpro 1512, HR 5, Kelig 100, Kelig 400, Lignopol, Lignosite 431, Lignosite 458, Lignosite 854, Lignosol, Lignosol AXD, Lignosol D 10, Lignosol DXD, Lignosol FTA, Lignosol NSX 110, Lignosol SFX 65, Lignosol X, Lignosol X 50, Lignosol XD, Lsu, Maracell C, Maracell E, Maracell XC 2, Maracell XE, Marasperse B, Marasperse CBA 1, Marasperse CBO, Marasperse CBOS 4, Marasperse CBS, Marasperse CBX 2, Marasperse N, Marasperse N 22, Neocobaltin PNA 11, Newkalgen RX-B, Norlig 12, Orzan CD, Orzan LS, Orzan S, Orzan SL 50, Pearllex CP, Pearllex N, Peritan NA, Polyfon, Polyfon F, Polyfon H, Polyfon HUN, Polyfon O, Polyfon T, Pozzolith 100XR, Pozzolith 70, Raycote, Raylig 260LR, Raymix, Reax 05A, Reax 45A, Reax 80C, Reax 81A, Reax 82, Reax 825E, Reax 83A, Reax 83C, Reax 85A, Reax 85C, Reax 88B, Reax 905, Reax 95A, Reax 98B, Reax SR 1, Reveal NM, Reveal SM, Reveal SM 5, Reveal WM, San-X P 213, San-X P 252, San-X P 550, San-X P 552, Sanekis P 550, Sanflo GR, Sodalig, Ufoxane 2, Ufoxane 3, Ufoxane 3A, Ultramix, sodium lignin sulfonate, Temsperse P 2000, Temsperse S 001, UF 10000A, Vanillex HW, Vanillex N, Vanisperse A, Wanin S, Wanin SR, sodium lignosulfite, Ultrazine NA, Ultrazine NAS, Urzan S, Vanicell, sodium lignosulfonic acid, sodium lignosulfonate, Zewa EF 220, Zewa S 210, Zewa SL, sodium lignosulfonic acids, and sulfonated lignin sodium salt. Under a preferred aspect of the present embodiment, modified lignins are obtained by treatment with alkali or by sulfonation. Such modified lignins are obtained as by-products derived from the wood pulping process. Preferably, the dispersant is a lignosulfonate salt, for example, sodium lignosulfonate salts such as Reax 88B, Reax100M, Polyfon H, Polyfon O, Polyfon T, or Polyfon F, available from MeadWestvaco Corporation and Ufoxane 3A, available from LignoTech USA, Inc., or a calcium lignosulfonate salt, for example, Norlig BD, available from LignoTech USA, Inc. The lignosulfonate salt can be used in combination with the sodium salt of a substituted naphthalene sulfonate formaldehyde polymer. An example of a suitable sodium salt of a substituted naphthalene sulfonate formaldehyde polymer is Morwet D-425 powder, available from Akzo Nobel. In one of the preferred aspects of the present embodiment, the lignin is a highly sulfonated hybrid kraft lignin. In another aspect the lignin is selected from the group consisting of Reax 88A, Reax 88B and Reax 100M, all available from MeadWestvaco Corporation. In yet another aspect, the lignin is Reax 88B.

The polymeric dispersant typically is well mixed with water. The water can be from any source and may contain any excipients or impurities, as long as the excipients or impurities do not interfere with the effective encapsulation of the clomazone in microcapsules, do not interfere with the spray-drying process, and do not otherwise interfere with other compositions in a way that would lower the loading level or effectiveness of the clomazone formulation. Under a preferred aspect of the present embodiment, the water is tap water. Under another aspect of the present embodiment the water is pure water, which may be obtained by filtration, distillation, reverse osmosis, direct membrane distillation, or the like.

In one aspect of step (i), the temperature of the resulting water mixture may be raised by an amount sufficient to aid the dissolution or homogeneous suspension of the components in the water.

Any organic solvent that easily dissolves or suspends clomazone, and that is immiscible with water, is suitable in the present embodiment. Among suitable water-immiscible inert organic solvents in which clomazone may be dissolved are mixtures of mono- and polyalkylated aromatics commercially available from Shell Oil Co. under the trademark SHELLSOL; various petroleum fluids available from Exxon such as Aromatic 200, AE700, and Exxate 700; various fatty acid methyl esters available from Henkel Corporation, such as Emery 2209, Emery 2270, and Emery 2301; and edible oils such as soy bean oil, corn oil, sunflower oil, vegetable oil, peanut oil, and canola oil. Organic solvents that are useful in the present method include methylene chloride, chloroform, ethyl acetate, cyclopentane, pentane, 2-methylbutane, methylcyclopentane, methylcyclohexane, benzene, cyclohexene, ethyl vinyl ether, 1,2-epoxybutane, furan, tetrahydropyran, fluorobenzene, hexafluorobenzene, ethyl propionate, methyl methacrylate, chloroethane, 1-chloro-2-methylpropane, 2-chloro-2-methylpropane, 1-chloro-3-methylbutane, 3-chloropropene, tetrachloromethane, 1,1-dichloroethane, 1,2-dichloroethane, 1,2-dichloropropane, 1,1-dichloroethylene, 1,2-dichloroethylene, trichloroethylene, 2-bromo-2-methylpropane, 1,1,2-trichloro-1,2,2-trifluoroethane, 1,1,2,2-tetrachlorodifluoroethane, 1,2-dibromotetrafluoroethane, 1,2-dibromo-1,1-difluoroethane, 1,1-dichloro-2,2-difluoroethylene, and the like. Any of these solvents can be used alone or in a mixture with any one or more of the other solvents.

The organic solvent of the present embodiment may also be an animal fats or oils, or a vegetable oil. Vegetable oils usable in the present embodiment can be any lipid materials derived from plants, provided that the lipid material is immiscible with water, the lipid material easily dissolves clomazone, and the lipid material does not contain chemical groups reactive to isocyanates such as amines, alcohols, free acids, and the like. Chemically, vegetable oils may be described as triglycerides. Under one aspect of the present embodiment, the vegetable oil contains a mixture of triglycerides, diglycerides, monoglycerides, free fatty acids and unsaponifiable lipids. Suitable vegetable oils within the scope of the present embodiment include edible oils, biofuel oils, drying oils, and other oils that are of plant origin. The edible oils usable in the present embodiment include almond oil, avocado oil, coconut oil, corn oil, cottonseed oil, diacylglycerol (DAG) oil, ghee, grape seed oil, groundnut oil, hemp oil, lard, margarine, mustard oil, olive oil (including extra light, virgin, extra virgin, and refined), palm oil, peanut oil, rapeseed oil, canola oil, rice bran oil, safflower oil, sesame oil (including semi-refined and unrefined), soybean oil, sunflower oil (including high oleic, and linoleic), tea seed oil, and walnut oil. Biofuel oils usable in the present embodiment include castor oil, coconut oil, colza oil, corn oil, cottonseed oil, false flax oil, hemp oil, mustard oil, palm oil, peanut oil, radish oil, rapeseed oil, ramtil oil, rice bran oil, safflower oil, salicornia oil, soybean oil, tigernut oil, tung oil, copaiba, honge oil, jatropha oil, jojoba oil, milk bush, nahor oil, paradise oil, and petroleum nut oil. Drying oils usable in the present embodiment include dammar oil, flaxseed oil, linseed oil, poppyseed oil, stillingia oil, tung oil, and vernonia oil.

In one preferred embodiment, the organic solvent may also be an herbicidally effective compound such as metolachlor.

The solution in step (ii) of the above method of preparing an aqueous suspension of microcapsules may include additional herbicidally effective compounds. In one preferred embodiment, the additional herbicidally effective compound is sulfentrazone.

In addition to clomazone and an organic solvent, the solution in step (ii) of the above method of preparing an aqueous suspension of microcapsules also includes a polyisocyanate. The term "polyisocyanate" means a mixture of compounds that contain on average two or more isocyanate groups per molecule. Preferred isocyanates are mostly a mixture of di- and triisocyanates of which the isocyanate groups may be linked to an aliphatic or aromatic moiety. Examples of suitable aliphatic di- and triisocyanates are tetramethylene diisocyanate, pentamethylene diisocyanate, hexamethylene diisocyanate and 4-(isocyanatomethyl)-1,8-octyl diisocyanate. Suitable aromatic isocyanates are toluene diisocyanate (TDI), polymethylene polyphenylisocyanate (MDI); 2,4,4'-diphenyl ether triisocyanate; 3,3'-dimethyl-4,4'-diphenyl diisocyanate; 3,3'-dimethoxy-4,4'-diphenyl diisocyanate; 1,5-naphthalene diisocyanate; 4,4',4"-triphenylmethane triisocyanate; and mixtures thereof. A further suitable diisocyanates include is isophorone diisocyanate. Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol. In this way several molecules of diisocyanate are linked via urethane groups to the polyhydric alcohol to form high molecular weight polyisocyanates. Another suitable product of this kind can be prepared by reacting three moles of toluene diisocyanate with one mole of 2-ethylglycerol (1,1-bismethylolpropane). Further suitable products are obtained by addition of hexamethylene diisocyanate or isophorone diisocyanate to ethylene glycol or glycerol. Preferred polyisocyanates are diphenylmethane-4,4'-diisocyanate and polymethylene polyphenylisocyanate. The di- and triisocyanates specified above can be employed individually or as mixtures of two or more such isocyanates.

Under a preferred aspect of the present embodiment the polyisocyanate is with functionality of more than 2 and less than 3. Examples of suitable polyisocyanates include PAPI® 27, PAPI® 94, PAPI® 95, PAPI® 901, PAPI® PB 219, Rubinate® M, Rubinate® 1245, Rubinate® 1820, Rubinate® 9016, Rubinate® 9257, Rubinate® 9259, Rubinate® 9041, Rubinate® 9236, Suprasec® 5025, Suprasec® 9615, Suprasec® 9582, Suprasec® 9611, Suprasec® 9584, Suprasec® 9610, Suprasec® 2496, Suprasec® 9600, Mondur® 1508, Mondur® 486, Mondur® 448, Mondur® MRS, Mondur® MR, Mondur® 489, Mondur® 582, Mondur® MRS-5, Mondur® MR-5, Mondur® MRS-4, Mondur® MRS-2, Lupranate® M10, Lupranate® 82500, Lupranate® M20, Lupranate® M20FB, Lupranate® M20HB, Lupranate® M20SB, and Lupranate® M70L. In a further aspect of the present embodiment, the polyisocyanate has a functionality of between 2.5 and 2.8.

Under a further aspect of the present embodiment, the temperature of the organic solution of at least clomazone, inert organic solvent and polymeric polyisocyanate is raised by an amount sufficient to aid the dissolution of the components or to aid homogenization of suspension of the components in the organic solution. Because of the potential of dimerization of the suitable polyisocyanate or oligomerization of the suitable polyisocyanate with itself, the temperature of the organic solution is not to be raised above the temperature at which dimerization or oligomerization is found to occur.

The addition of the organic solution to the aqueous solution generates a mixture of two separate immiscible phases. In order to prepare microencapsulated clomazone, this mixture is emulsified. The emulsification step, step (iii) of the above method of preparing an aqueous suspension of microcapsules, requires high shear mixing to give small droplets of the immiscible phase. This process generates an oil-in-water emulsion. The discontinuous phase of the emulsion, i.e., the droplets, contains generally clomazone, organic solvent and polyisocyanate, while the continuous phase contains water and polymeric dispersant. Factors that influence droplet size, which determines the eventual size of the microcapsules, as well as the stability of the emulsion, depend on large part on the amount of energy delivered to the mixture, and include speed and length of mixing, the identity of the organic solvent, temperature, and viscosity. Selection of the appropriate microcapsule size to achieve a combination of low volatility and high suspensibility requires a balance between competing factors. In general, increasing microcapsule size decreases volatility, but also decreases suspensibility of the particles, while decreasing size yields better suspensibility, but higher volatility. For the purposes of the present embodiment the average size of the microcapsules is 1 to 50 microns, preferably 5 to 30 microns. The operating conditions to yield microcapsules of a desired size will depend on the emulsifying equipment used and the temperature, and adjustment of these and other relevant factors to determine the proper conditions is well within the skill of the art.

After the formation of the emulsion, a polyfunctional amine is added to the emulsion, to produce a plurality of microcapsules containing clomazone and organic solvent. In contrast to the conditions of the emulsification step, agitation during the amine addition should be gentle. Suitable polyamines means in general those compounds that contain two or more primary amino groups in the molecule, and which amino groups may be linked to aliphatic or aromatic moieties. Examples of suitable aliphatic polyamines are alpha, omega-diamines of the formula $H_2N(CH_2)_nNH_2$, wherein n is an integer from 2 to 6. Examples of such diamines are ethylenediamine, propylene-1,3-diamine, tetramethylene-diamine, pentamethylenediamine and hexamethylenediamine. A preferred diamine is hexamethylenediamine, specifically, 1,6-hexamethylenediamine.

Further suitable aliphatic polyamines are polyethyleneamines of the formula $H_2N(CH_2CH_2NH)_nH$ wherein n is an integer from 2 to 5. Representative examples of such polyethyleneamines are: diethylenetriamine, triethylenetriamine, tetraethylenepentamine, and pentaethylenehexamine.

Suitable aromatic polyamines are any aromatic polyamines that are water-soluble in a sufficient amount to react with the polyisocyanate. Examples of suitable aromatic polyamines include 1,3-phenylenediamine, 2,4-toluenediamine, 1,5-diaminonaphthalene, 1,3,5-triaminobenzene, 2,4,6-triaminotoluene, 1,3,6-triaminonaphthalene, 2,4,4'-triamino-diphenyl ether, 3,4,5-triamino-1,2,4-triazole, bis (hexamethylenetriamine), and 1,4,5,8-tetraminoanthraquinone. For those polyamines which are insufficiently soluble, the solubility may be improved by increasing the temperature of the solution, or by using the polyamines as salt adducts. The salt adducts which are suitable are those which do not interfere with the formation of the polyurea shell.

Yet further suitable polyamines are those that contain sulfo or carboxyl groups in addition to the amino groups. Examples of such polyamines are 1,4-phenylene diamine-sulfonic acid, 4,4'-diaminodiphenyl-2-sulfonic acid, or diaminoammocarboxylic acids such as ornithene and lysine.

The polyisocyanate, which is soluble in the discontinuous phase of the emulsion, and the polyfunctional amine, which is soluble in the continuous phase of the emulsion, react in the presence of the dispersant under proper agitation and reaction conditions to form microcapsules having polyurea walls encapsulating the core comprising the herbicidally active ingredient. The rate of polymerization will depend on the reaction conditions employed. The rate of polymerization will generally be related to the temperature at which the reaction takes place. The encapsulation process is capable of satisfactory performance and production of encapsulated material without adjustment to a specific pH value.

After the addition of the polyfunctional amine stirring is continued while the suspension is cured by heating the mixture to a temperature of about 35° C. to about 60° C., preferably about 45° C. to about 50° C., for 3 to 10 hours, preferably 4 to 5 hours.

The above procedure produces a plurality of microcapsules dispersed in an aqueous phase. The microcapsules comprise a polyurea shell, and a liquid core. The encapsulated liquid core contains the solution of at least the organic solvent oil and clomazone. The liquid core is similar in composition to the composition of the organic solution in the above method, except for the partial or complete absence of unreacted polyisocyanate. Clomazone has limited solubility in water (1100 ppm), thus a small amount of clomazone will be present in the aqueous phase, but this is not significant enough to have any non-de minimis effects on the loading level in the microcapsule.

In order to obtain a high loading level of clomazone in a commercially viable herbicidal composition, in one aspect of this embodiment, the loading level of clomazone with respect to the encapsulated material is as high as possible, preferably above 80 weight percent. The loading level of clomazone in the encapsulated material is determined by performing an analysis of the encapsulated material of the microcapsules. Alternatively, the loading level of clomazone in encapsulated material may be calculated based on the ratio of clomazone to the sum of non-reactive components of the solution in step (ii) of the above procedure.

After the formation of microcapsules, the herbicidal composition may then be formulated further by addition of various excipients, including density modifiers, viscosity modifiers, pH modifiers, or the like. For example, the homogeneous dispersions of polymer microencapsulated pesticides in water with an effective emulsifier, such as lignosulfonate, may be blended with a suspension system composition. If it is desired to adjust the pH of the finished microcapsule formulation as, for example, when the aqueous base formulation of the microcapsules is combined with other herbicides, fertilizers, etc., conventional and suitable reagents for pH adjustment may be used. Such reagents include hydrochloric acid, acetic acid, phosphoric acid, sodium hydroxide, potassium hydroxide, etc.

The dispersion may further comprise a combination of agents, such as surfactants, dispersants, antifreeze agents, clays, water, biocides, salts, polymers, thickeners, and other suspension stabilizing and density balancing agents, appropriately selected to keep the microcapsules in stable homogeneous suspension in the water-based carrier over an extended period of time. The agents comprising the dispersion will generally comprise 1 percent by weight to 15 percent by weight of the dispersion and preferably 2 percent by weight to 10 percent by weight. In order to process and apply the herbicide in a uniform manner, the dispersion is preferably homogeneous.

The dispersion may also include a small amount of a xanthan gum thickening agent in combination with ammonium sulfate to aid in stabilizing the dispersion of the microcapsules. The gum is preferably present in an amount in the range from about 0.01 percent by weight to about 0.1 percent by weight of the dispersion although greater or lesser amounts may be employed. The ammonium sulfate is preferably present in an amount in the range from about 3 percent by weight to about 17 percent by weight of the dispersion, more preferably in the range from 5 percent by weight to 10 percent by weight, although amounts outside of these ranges may be employed.

As discussed above, one way of increasing the overall loading level of clomazone in an aqueous herbicide comprising microencapsulated clomazone is to increase the loading level of the clomazone in the encapsulated material. Another way of increasing the overall loading level of an aqueous herbicide comprising microencapsulated clomazone is to increase the loading level of the microcapsules in the dispersion. According to this aspect of the present embodiment, the increase of the portion of microcapsules in the dispersion is achieved by minimizing the amount of water or other solvents that are typically added to the dispersion after the formation of the microcapsules when excipients are added (for example, xanthan gum is typically added into an agricultural formulation by slurrying the xanthan gum with water prior to adding it to the herbicide). The present embodiment is also directed to the addition of excipients in powdered form instead of as an aqueous solution or mixture. A viscosity modifier, such as xanthan gum, is added as a powder to the aqueous suspension of microcapsules. A density modifier, such as ammonium sulfate, is added as a powder to the aqueous dispersion of microcapsules. Alternatively, the density modifier and viscosity modifier can be mixed together as a powder, and may be added to the aqueous suspension together. Excipients may also be added to the aqueous dispersion of microcapsule in a powdered form either step-wise or mixed together prior to addition. Such an addition of excipients as a dry mix eliminates the unwanted introduction of diluting water.

In one particularly preferred aspect of this embodiment, the organic solvent used in step (ii) of the above process is linseed oil. The use of linseed oil allows surprisingly and unexpectedly high loading levels of clomazone. According to this aspect, in microcapsules encapsulating a solution of linseed oil and clomazone, clomazone may contain 80 to 97 weight percent of the encapsulated solution. This loading level of clomazone is greater than in the previously disclosed or commercially available microencapsulated clomazone. According to this aspect, the clomazone may comprise 85 to 97, 90 to 97, or 95 to 97 weight percent of the encapsulated solution. In order to achieve such high loading levels of clomazone, care should be taken to select the appropriate reaction conditions, which are within the reach of an ordinary person skilled in the art; such conditions may include minimizing addition of any other excipients and increasing the purity of the clomazone starting material. To achieve the highest levels of clomazone loading levels, very high purity clomazone should be used, and no excipients should be added to the solution of clomazone, linseed oil and polyisocyanate in step (ii).

The loading level of clomazone with respect to the encapsulated material should be high as possible; however, above a certain loading level, the preparation of the microcapsules fails. Specifically, when polyfunctional amine is added to the emulsified mixture containing clomazone and linseed oil, wherein clomazone is over this certain limit, the emulsified mixture gels, and microcapsules form poorly. By adjusting for purity of clomazone, the upper limit of clomazone loading level is between 91.4 and 93.0 weight percent. However, by not adjusting for the purity of clomazone, the upper limit of clomazone loading level in the core material in formulations A through H (in the Examples below) is between 96.2 and 98.1 weight percent, which is indicative of the high loading level of clomazone achievable if highly pure clomazone is used in the process.

The aqueous solution comprising a plurality of microcapsules may be used in any acceptable use known in the art. For instance, an herbicidally effective amount of such microcapsules may be applied to an agricultural field, after which application ambient water will be able to continuously penetrate the polyurea shell, dissolving small amounts of clomazone, and diffusing the clomazone-water solution out of the microcapsule into the agricultural field. This aspect may be used to control weeds comprising applying an herbicidally effective amount of the herbicidal composition of any of the above compositions to an area where weeds are present. The preferred plants that are controlled by this method include grasses and broadleaves. Specifically, the weeds may be controlled by this method include those selected from the group consisting of barnyard grass, broadleaf signalgrass, crabgrass, foxtail, goosegrass, *panicum*, Johnsongrass, cupgrass, field sandbar, Bermuda grass, red rice, itch grass, velvetleaf, spurred anoda, common ragweed, Jimsonweed, Lambsquarter, Pennsylvania smartweed, prickly *sida*, purslane, redweed, Venice mallow, cocklebur, dayflower, Florida beggarweed, Florida pusley, Kochia, redvine, tropic *croton*, wild pointsettia, balloonvine, black nightshade, curly dock, joint vetch, and morning glory.

Various aspects of the embodiment are illustrated and explained in more detail in Examples 1-3, wherein parts and percentages are given on a weight basis unless otherwise stated. It should be understood that the examples are merely illustrative of the embodiment and not limitative.

High Loading Dry Formulation Containing Microcapsules of Clomazone

Various methods of microencapsulating clomazone are disclosed in U.S. Pat. Nos. 5,583,090; 5,597,780; 5,783,520; 6,380,133; 6,440,902; RE38,675; and U.S. Patent Publication No. 2010/0234225. A process for microencapsulating clomazone is also described above in the present disclosure. According to the present embodiment, aqueous encapsulated clomazone compositions may be further coated with a water-soluble polymer. A high-clomazone-loaded solid composition of microcapsules has been prepared which are comprised of a core comprising clomazone, surrounded by a polyurea shell, which in turn is surrounded by a coat comprised of water-soluble polymer. Such a composition may be prepared by spray-drying an aqueous suspension of microencapsulated herbicide in the presence of a polyvinyl alcohol. The dry composition comprises about 5 to 20 weight percent polyvinyl alcohol.

One of the advantages of the present embodiment is lower costs associated with the manufacture, storage, transportation, and use of the herbicide. By increasing the loading level of an herbicidally active ingredient, the total mass and total volume of the herbicide that is used in an agricultural field decreases for a given amount of the herbicidally active ingredient. Increasing the loading level of the herbicidally active ingredient and decreasing the loading levels of the inert ingredients present in the herbicide, decreases the overall volume and weight of the herbicide, resulting in lower production costs, lower packaging costs, lower transportation costs, lower storage costs, lower handling costs, and general lowering of other costs associated with making, storing, transporting, and using the herbicide.

Another advantage provided by the present embodiment is the ease of cleaning up accidental spills of the herbicide. Accidental spills of solutions of aqueous microencapsulated herbicides are difficult and costly to clean up. Countermeasures against accidental releases include the use of dikes to confine the spill, use of absorbents, and neutralization of the area by a solution of potassium hydroxide in methanol. In addition, cleaning up a spill of a liquid generates lots of waste material. Under certain conditions any soil contaminated with aqueous microencapsulated herbicide needs to be remediated; such remediation may include excavation and hauling of the contaminated soil to a landfill, and other expensive techniques. Switching from the aqueous microencapsulated form of clomazone-based herbicide Command® 3ME to the solid form of clomazone-based herbicide drastically reduces the above-listed costs, in part due to the doubling of the loading level of clomazone in the herbicide.

One of the aspects of the present embodiment is to provide a method for preparing a herbicidal composition that comprises a solid form of a microencapsulated herbicide. The process for preparing the solid form of the microencapsulated herbicide comprises the steps of (a) preparing an aqueous suspension of microcapsules comprising a polyurea shell surrounding a core comprising clomazone dissolved in an inert organic solvent; (b) adding water-soluble polymer to the aqueous suspension, and (c) spray-drying the resulting mixture.

This method generates a solid form of a clomazone-based herbicidal composition. This solid form may be a powder form, or granular form, or particulate form, or a continuous solid. In a preferred embodiment, the solid form is flowable, so that the solid herbicide can be poured from one container to another. The microcapsules, which are comprised of a polyurea shell and a core containing clomazone, are surrounded by water-soluble polymer. In one embodiment, the water-soluble polymer is of uniform thickness, surrounding the microcapsules evenly. In another embodiment the thickness is not uniform, but is influenced by the packing of the neighboring microcapsules and other effects. Under yet another embodiment at sufficiently high enough loading levels of water-soluble polymer, the water-soluble polymer forms a continuous matrix in which the microcapsules are embedded.

The solid form of a microencapsulated herbicide described above is water-dispersible. When the solid form is used on an agricultural field, the user measures out the appropriate amount of the herbicide into a farm tank, a spray tank or a similar container, in which the herbicide is mixed with water to generate an aqueous suspension of the microcapsules. The water-soluble polymer coat surrounding the shell dissolves in the water, releasing the microcapsules into the water to form an aqueous mixture, which is suitable for spraying onto a field. The aqueous mixture may also contain other ingredients, such as insecticides, fungicides, rodenticides, nemocides, defoliants, and adjuvants such as salts used to adjust the density of the aqueous mixture.

The process for preparing the above solid form comprises a step of preparing an aqueous suspension of microcapsules comprising a polyurea shell surrounding a core comprising clomazone dissolved in an inert organic solvent. The preparation of an aqueous suspension of microcapsules comprising a polyurea shell surrounding a core comprising clomazone dissolved in an inert organic solvent may be undertaken by any of the known microencapsulation techniques, including the technique described in the present disclosure. In one aspect of the present embodiment, the preparation follows any technique which is suitable to generate a microencapsulated formulation suitable for use as an aqueous microencapsulated herbicidal product. In another aspect, adjuvants, such as salts that are used to adjust the density in order to aid suspension of the microcapsules or such as acids or bases that are used to adjust the pH of the suspension of the microcapsules, are omitted from the steps used to prepare the aqueous suspension of microcapsules. This aspect, ceteris paribus, results in a solid herbicidal product with higher loading levels of clomazone. Under an alternative aspect, adjuvants similar to those used in preparation of aqueous microencapsulated clomazone are added to the aqueous suspension of microcapsules. Under this aspect the adjuvants aid in mixing of the solid herbicidal product in the mixing tank.

In a further aspect of the present embodiment, the aqueous suspension of microcapsules comprising a polyurea shell surrounding a core comprising clomazone dissolved in an inert organic solvent may next be treated with water-soluble polymer. The water-soluble polymer may be added to the aqueous suspension of microcapsules either in a solid form, or dissolved in water prior to addition to the aqueous suspension.

Any of a number of commonly utilized water-soluble polymers may be employed. Suitable water-soluble polymers include polyacrylamides, polyvinyl alcohol, polyacrylic acid, polyacrylates, casein, gelatins, polyamines, acrylamide-dimethylaminoethyl acrylate copolymers, polyethyleneimines, polyamidoamines, polyvinylpyrrolidones, polyethylene glycols, methylcellulose, alginates, caroxymethylcellulose, xanthan, pectin, carrageenan, carboxypolyethylene, and agar. The water-soluble polymer used in construction of the coat may be non-ionic, anionic, cationic, or amphoteric. The water-soluble polymer may be a block polymer, or a random polymer. The water-soluble polymer may be added to the aqueous suspension in any of the commonly encountered physical forms of the water-soluble polymer, including emulsions, solutions, powders, and beads.

One preferred water-soluble polymer is polyvinyl alcohol. Polyvinyl alcohol is usually sold in solid form, in a number of variations of molecular weight and degree of hydrolysis. In general, polyvinyl alcohol of lower molecular weight or lesser degree of hydrolysis tends to be more water-soluble, and thus is more preferred. For instance, partially hydrolyzed polyvinyl alcohols (e.g., up to about 89 to 90% hydrolyzed) tend to be more water-soluble and thus more preferred for use in this embodiment.

For example, of the Celvol® line of polyvinyl alcohols available from Celanese Corporation, a preferred polyvinyl alcohol is Celvol® 203. It is 87 to 89% hydrolyzed, may be dissolved in water to form solutions of up to 30% polyvinyl alcohol by weight, and has a viscosity of 3.5 to 4.5 cps (4% aqueous solution, 20° C.). Two other products, Celvol® 103 and 107, have a higher degree of hydrolysis (98 to 98.8%) but a lower molecular weight. They would also be suitable for use in the present embodiment but products produced from them would tend to disperse more slowly in water.

Under one aspect of the present embodiment, the weight ratio of the water-soluble polymer to clomazone is from about 1:6 to about 1:4. This means that the weight of the water-soluble polymer as added to the aqueous solution is about one sixth to about one quarter the weight of clomazone used in preparing the organic solution for the microcapsule preparation.

In addition to the polymeric dispersant and a water-soluble polymer, the aqueous phase may further comprise a salt. Upon evaporation of the water by a spray dryer, the optional salt will be incorporated into the coat surrounding the microcapsule. One of the functions of adding a salt to the suspension of the microcapsules in water comprising water-soluble polymer, is to aid in formation of the microcapsule coat. Another function of adding a salt to the suspension of the microcapsules in water comprising water-soluble polymer, is to aid in dispersion of the solid herbicidal composition in water upon addition to a water tank. Still another function of adding a salt to the aqueous phase is to aid in mixing the dispersed microcapsules in a mixing tank by adjusting the density of the water solution of the mixing tank with the density of the microcapsules. If the mean densities of microcapsules and the aqueous phase are approximately equal, the microcapsules tend to be suspended in the aqueous phase more easily.

Any of the water-soluble salts are appropriate in this process. Most appropriate are salts that exhibit one or more of the above-identified functions. Examples of appropriate salts are common inorganic salts. Appropriate salts are those that are easily water-soluble and that are selected from the group consisting of alkali metal halide, alkaline earth metal halide, ammonium halide, alkali metal sulfate, alkaline earth metal sulfate, ammonium sulfate, alkali metal nitrate, alkaline earth metal nitrate, ammonium nitrate, alkali metal carbonate, and ammonium carbonate. Examples of alkali metal halides include LiCl, LiBr, LiI, NaCl, NaBr, NaI, KF, KCl, KBr, KI, RbF, RbCl, RbBr, and RbI. Examples of alkaline earth metal halides include $MgCl_2$, $MgBr_2$, $MgI_2$; $CaCl_2$, $CaBr_2$, $CaI_2$, $SrCl_2$, $SrBr_2$, $SrI_2$, $BaCl_2$, $BaBr_2$, and $BaI_2$. Examples of ammonium halide include $NH_4F$, $NH_4Cl$, $NH_4Br$, and $NH_4I$. Examples of alkali metal sulfate are $Li_2SO_4$, $Na_2SO_4$, $K_2SO_4$, and $Rb_2SO_4$. An example of an alkaline earth metal sulfate is $MgSO_4$. Ammonium sulfate is $(NH_4)_2SO_4$. Examples of alkali metal nitrate include $LiNO_3$, $NaNO_3$, $KNO_3$, and $RbNO_3$. Examples of alkaline earth metal nitrate include $Mg(NO_3)_2$, $Ca(NO_3)_2$, and $Sr(NO_3)_2$. Ammonium nitrate is $NH_4NO_3$. Examples of alkali metal carbonate include $Na_2CO_3$, $K_2CO_3$, and $Rb_2CO_3$. Ammonium carbonate is $(NH_4)_2CO_3$.

The aqueous solution of water-soluble polymer, polymeric dispersant, optional salt, and suspended microcapsules comprising clomazone dissolved in organic liquid and polyurea shell, as obtained by the process steps above, is spray dried by commonly used techniques. Spray drying converts the aqueous solution into a solid comprising a core comprising clomazone and organic liquid, surrounded by a polyurea shell, which in turn is surrounded by a coat, by rapidly drying the introduced stream of the aqueous solution with a hot gas. The coat comprises the solutes of the aqueous solution. The use of spray drying is the preferred method to other methods of removing water from liquids to obtain solids, because spray drying results in a consistent particle size distribution. Air is the heated drying medium.

After collecting the solid herbicidal composition, the composition may be ground, screened, and bagged, or otherwise used further for forming an herbicide. Grinding and screening aids in delivering a uniform product to the end user, or aids in dissolution in a mixing tank. Care must be taken that grinding does not deleteriously affect the microcapsule coat.

One of the aspects of the present embodiment is a microcapsule comprising a core surrounded by a shell which is surrounded by a coat, which may be obtained by any of various processes. In this aspect, the core comprises clomazone dissolved in an inert organic solvent; the shell comprises polyurea; the coat comprises a water-soluble polymer; and wherein clomazone comprises 50 weight percent or more of the microcapsule. The definitions of the components, choice of loading levels, and other parameters can be selected for the corresponding components above.

It is surprising and unexpected that small changes in the loading levels of the shell-forming ingredients (polyisocyanate and polyfunctional amine) and polyvinyl alcohol have a sizeable effect on the volatility of the formulation. Formulation A (below), with weight ratios of core:shell:coat equal to 300:50:50 exhibited volatility similar to, or slightly better than, that of the commercial product Command® 3ME. On the other hand, Formulation B (below), with weight ratios of core:shell:coat equal to 300:64:56 exhibited volatility of about one quarter of that of the commercial product Command® 3ME.

Under one aspect of the microcapsule of the present embodiment, the weight ratio of the water-soluble polymer to clomazone is from about 1:6 to about 1:4. This means that the weight of the water-soluble polymer as added to the aqueous solution is about one sixth to about one quarter the weight of clomazone used in preparing the organic solution for the microcapsule preparation. In an alternate aspect, this means that the weight of clomazone determined analytically from a sample of the solid herbicidal composition is about four to six times the weight of the water-soluble polymer in the sample of the dry herbicidal composition.

Suitable water-soluble polymer use in the present application is any water-soluble polymer that controls the volatility of clomazone. One of the preferred water-soluble polymers is polyvinyl alcohol.

In one aspect, clomazone is present in the herbicidal composition in an amount from about 50 percent by weight to about 80 percent by weight. Under another aspect, clomazone is present in the herbicidal composition in an amount from about 55 percent by weight to about 70 percent by weight.

Under one aspect of the present embodiment, the weight ratio of the sum of the weights of polyisocyanate and polyfunctional amine to the weight of polyvinyl alcohol is between about 3:1 to about 1:3. Under another aspect of the present embodiment, the weight ratio of the sum of the weights of polyisocyanate and polyfunctional amine to the weight of polyvinyl alcohol is between about 1.5:1 to about 1:1.5.

A further aspect of the present embodiment is a solid herbicidal composition comprising microcapsules which comprise a core surrounded by a shell which is surrounded by a coat, which may be obtained by any of various processes. One aspect of the present embodiment is a solid herbicidal composition comprising a plurality of microcapsules comprising a core surrounded by a shell which is surrounded by a coat, which is obtained by the process described above. The description of the composition components, their loading levels, etc. can be determined by the teachings above.

Another aspect of the present embodiment is a method of controlling weeds comprising applying a herbicidally effective amount of any of the above herbicidal compositions to an area where weeds are present. The preferred plants that are controlled by this method include grasses and broadleaves. Specifically, the weeds that this method of applying herbicide with are selected from the group consisting of barnyard grass, broadleaf signalgrass, crabgrass, foxtail, goosegrass, *panicum*, Johnsongrass, cupgrass, field sandbar, Bermuda grass, red rice, itch grass, velvetleaf, spurred anoda, common ragweed, jimsonweed, lambsquarter, Pennsylvania smartweed, prickly *sida*, purslane, redweed, Venice mallow, cocklebur, dayflower, Florida beggarweed, Florida pusley, kochia, redvine, tropic *croton*, wild pointsettia, balloonvine, black nightshade, curly dock, joint vetch, and morning glory.

The above herbicidal compositions may be applied alone or in a tank mix combination by ground equipment using a finished spray volume of 100 to 400 L/ha (10 to 40 gal/acre). The herbicide comprising the herbicidal composition is suitable for applications using nozzles suitable for broadcast boom or banded application of the herbicide. Nozzle screens and strainers should be no finer than 300 microns (50 mesh). The herbicide comprising the herbicidal composition may be used as a preemergent soil-surface-applied treatment from 30 days before planting to just prior to crop emergence. If field conditions indicate the need for additional seedbed preparation, the use of equipment which will move the herbicide no deeper than 4 to 5 cm (1.5 inches to 2 inches) is acceptable.

The minimal broadcast rate for velvetleaf or spurred anoda is 560 g/ha (0.50 lb/acre) of herbicidally active ingredient clomazone. The minimal broadcast rate for barnyard grass, broadleaf, signalgrass, crabgrass, foxtail, goosegrass, *panicum*, Johnsongrass; common ragweed, jimsonweed, lambsquarter, Pennsylvania smartweed, prickly *sida*, purslane, redweed, or Venice mallow is 840 g/ha (0.75 lb/acre) of the herbicidally active ingredient clomazone. The minimal broadcast rate for cupgrass, field sandbar, Bermuda grass, red rice, itchgrass, cocklebur, dayflower, Florida beggarweed, Florida pusley, Kochia, redvine, tropic *croton*, and wild pointsettia is 1.1 kg/ha (1.0 lb/acre) of the herbicidally active ingredient clomazone. The minimal broadcast rate for balloonvine, black nightshade, curly dock, joint vetch, and morning glory is 1.4 kg/ha (1.25 lb/acre) of the herbicidally active ingredient clomazone.

The present embodiment is illustrated and is explained in more detail in Examples 4-8, wherein parts and percentages are given on a weight basis unless otherwise stated. It should be understood that the examples are merely illustrative of the embodiment and not limitative.

Dry Formulations Containing Encapsulated Clomazone

In another embodiment, the present disclosure provides methods and materials for making water-dispersible dry granules containing encapsulated clomazone and one or more additional agriculturally active ingredients that have excellent physical and chemical stability and exhibit good volatility control of clomazone.

One aspect of the present embodiment is a method for making water-dispersible granules for delivering agricultural chemicals to a crop comprising the steps of:
 a) forming a water-dispersible powder of one or more agriculturally active agents,
 b) milling the water-dispersible powder,
 c) kneading an aqueous encapsulated clomazone composition into the milled water-dispersible powder to form a wetted powder,
 d) forming granules by subjecting the wetted powder to pan pelletization, and
 e) drying the granules.

Another aspect of the present embodiment is a method for making water-dispersible granules for delivering agricultural chemicals to a crop comprising the steps of:
 a) forming a water-dispersible powder of one or more agriculturally active agents,
 b) milling the water-dispersible powder,
 c) kneading an aqueous encapsulated clomazone composition into the milled water-dispersible powder to form a dough,
 d) extruding the dough to form granules, and
 e) drying the granules.

Another aspect of the present embodiment is a method for making water-dispersible granules for delivering agricultural chemicals to a crop comprising the steps of:
 a) forming a water-dispersible powder of one or more agriculturally active agents,
 b) milling the water-dispersible powder,
 c) kneading the milled water-dispersible powder with water to form a dough,
 d) extruding the dough to form granules,
 e) spray coating an aqueous encapsulated clomazone composition onto the granules in a Wurster Coating apparatus, and
 f) drying the coated granules.

Another aspect of the present embodiment is a method for making water-dispersible granules for delivering agricultural chemicals to a crop comprising the steps of:
 a) forming a water-dispersible composition of one or more agriculturally active agents,
 b) milling the water-dispersible composition,
 c) mixing the milled water-dispersible composition with an aqueous encapsulated clomazone composition, and
 d) spray drying the mixture to form granules.

Another aspect of the present embodiment is a method for the control of unwanted plants comprising applying a pesticidally effective amount of the compositions of the present embodiment to an area where such control is desired. The term "pesticidally effective amount" means an amount necessary to produce an observable pesticidal effect on unwanted plant growth, including the effects of necrosis, death, growth inhibition, reproduction inhibition, inhibition of proliferation, and removal, destruction, or otherwise diminishing the occurrence and activity of unwanted plants.

One or more agriculturally active agents can be combined with clomazone in this embodiment. It is preferred that the one or more agriculturally active agents that can be combined with clomazone, using the method of this embodiment, are herbicides. Preferably the herbicides are selected from the group consisting of aclonifen, the common name for 2-chloro-6-nitro-3-phenoxybenzeneamine; and napropamide, the common name for N,N-diethyl-2-(1-naphthalenyloxy)propanamide.

The water-dispersible powder containing one or more agriculturally active agents comprises one or more active agents; and one or more of a wetting agent, for example, sodium alkylbenzene sulfonate (STEPWET® DF-90 available from Stepan Company), or sodium alkylnaphthalenesulfonate formaldehyde polymer (MORWET® D-425 POWDER available from Akzo Nobel); a dispersant, for example, sodium lignosulfonate (POLYFON® O available from MeadWestvaco Corporation), naphthalene sulfonate condensate (AGNIQUE® NSC available from Cognis Corporation), sodium 2-[methyloleoylamino]ethane-1-sulfonate (GEROPON® T77 available from Rhodia Novecare), naphthalenesulfonic acid polymer with formaldehyde sodium salt (VULTAMOL® NH 7519 available from BASF Corporation or Atlox™ 4862 available from Crodia Crop Care), or modified sodium lignosulfonate (Ufoxane® 3A available from Borregaard Lignothech); a defoamer, for example, AGNIQUE® SOAP L (available from Cognis Corporation); and a carrier, for example, precipitated silica (for example, HiSil™ ABS from PPG Industries), ammonium sulfate or continental clay or mixtures thereof.

Various aspects of the embodiment are illustrated and explained in more detail in Examples 1-3, wherein parts and percentages are given on a weight basis unless otherwise stated. It should be understood that the examples are merely illustrative of the embodiment and not limitative.

Triple Formulation Containing Clomazone, Metolachlor, and Sulfentrazone

A microencapsulated formulation of clomazone, metolachlor, and sulfentrazone was prepared. Using metolachlor as the organic solvent for clomazone and sulfentrazone, it was possible to prepare the microencapsulated formulation according to the procedure described above. The ability to prepare a microcapsule containing only active ingredients allows production of a microcapsule suspension containing close to 40% total active loading, which gives good volatility control and efficacy. Furthermore, conventional formulation procedures when applied to mixtures of clomazone and sulfentrazone have not been able to produce commercially acceptable volatility or stability.

DEFINITIONS

As used in this application and unless otherwise indicated the term "herbicide" refers to a compositional mixture that is produced, sold, or used in a field in order to kill or otherwise inhibit unwanted plants such as, but not limited to, deleterious or annoying weeds, broadleaf plants, grasses, and sedges; and can be used for crop protection, edifice protection or turf protection. The term "herbicide" includes the end-use herbicidal product. This composition may be a pure compound, a solution of chemical compounds, a mixture of chemical compounds, an emulsion, a suspension, a solid-liquid mixture, or a liquid-liquid mixture. The term "herbicide" also refers to the product that passes through the commercial channels from the manufacturer to the ultimate end user who can either apply the herbicide to the affected field as sold, or mix it with other excipients.

The term "weed" means and includes any plant which grows where not wanted.

The term "herbicidally effective amount" means an amount necessary to produce an observable herbicidal effect on unwanted plant growth, including the effects of necrosis, death, growth inhibition, reproduction inhibition, inhibition of proliferation, and removal, destruction, or otherwise diminishing the occurrence and activity of unwanted plants.

The term "herbicidally active ingredient" means the active ingredient in the herbicide that causes the herbicide to prevent, destroy, repel or mitigate any weed. Other ingredients of the herbicide that are not herbicidally active ingredients are excipients that aid in forming, storing, or delivering herbicidally active ingredient to the target. Examples of excipients in the present embodiment include an organic liquid in which herbicidally active ingredient is dissolved, the polyurea shell, the water-soluble polymer, and salts.

The definition of the term "herbicidal composition" refers to an herbicide, and in addition, to any composition that comprises an herbicidally active ingredient. This composition may be a solution or a mixture. Further, the definition of the term "herbicidal composition" also refers to a product intended for use in manufacturing, or any product intended for formulation or repackaging into other agricultural products.

Clomazone is the common name for 2-(2-chlorophenyl) methyl-4,4-dimethyl-3-isoxazolidinone and is a highly effective herbicide.

The phrase "clomazone-containing herbicide" refers to an herbicide which comprises clomazone as one of the herbicidally active ingredients. Although Formulations A through F contain only clomazone as the herbicidally active ingredient, it is understood that the herbicidal composition may also comprise other herbicidally active ingredients.

The phrase "clomazone-containing herbicidal composition" refers to an herbicidal composition which comprises clomazone as an herbicidally active ingredient.

The term "microcapsule" refers to a roughly spherical microscopic particle consisting of a polymeric shell and an encapsulated material located within the shell.

The term "shell" refers to a hollow microscopic particle that has a roughly spherical shape. The function of a shell, as used in a microcapsule, is to keep the encapsulated material found within the shell generally separate from the material outside of the microcapsule. The shell is diffusible so that under appropriate conditions it will allow diffusion into or out of the microcapsule to occur.

The term "core" of a microcapsule refers to the encapsulated composition located within the shell.

The terms "volatility control" or "clomazone volatility control" refer to the result of the clomazone volatility test detailed in Example 7, with the reference compound being Command® 4EC (FMC Corporation). That is, Command® 4EC has 0% volatility control. A theoretical formulation that allowed no clomazone to evaporate would have 100% volatility control.

The term "acceptable volatility control," used in reference to a clomazone formulation, means a formulation that exhibits a % volatility control test result of greater than 75%, preferably greater than 78%, still more preferably greater than 80%, yet more preferably greater than 90%, and most preferably greater than 94%.

EXAMPLES

Unless otherwise specified in the examples: the clomazone used in Examples 1-3 below comprised 94.8 to 96.8% clomazone; the clomazone used in examples 4-7 below comprised 96% clomazone; and the clomazone technical used in Examples 8-16 below contained 96.3% clomazone, the aclonifen technical used contained 94.4% active ingredient and the napropamide technical used contained 96.0% active ingredient.

The examples serve only to illustrate the embodiments described and should not be interpreted as limiting since further modifications of the disclosed embodiments will be apparent to those of ordinary skill in the art. All such modifications are deemed to be within the scope of the invention as defined in the claims. It will be obvious to those of ordinary skill in the art that variations in the preferred and described formulations and methods may be used and that it is intended that the claimed invention may be practiced otherwise than as specifically described herein. Accordingly, this invention includes all modifications encompassed within the spirit and scope of the invention as defined by the claims that follow.

Example 1

Preparation of Clomazone-Linseed Oil Herbicidal Composition (Formulation A)

Technical grade clomazone (255 g, 94.8% pure), linseed oil (45 g), and polymethylene polyphenylisocyanate (31.5 g, PAPI® 27, Dow Chemical Company) were added to a beaker to yield an organic mixture. In a separate stainless steel blender cup, sodium lignosulfonate (7.2 g, Reax 88B, MeadWestvaco Corporation) was stirred vigorously with water (228 g) at high speed on a blender (Waring Commercial Blender, Model HGBSSSS6) to give an aqueous mixture. The temperature of both the aqueous mixture and the organic mixture was raised to 45° C. While held at that temperature, with the stirring stopped, the organic mixture was added to the aqueous mixture. After the addition was complete, the resulting mixture was mixed at high speed for 15 sec. The stirring was then reduced to a lower speed, and a 1,6-hexanediamine aqueous solution (31.2 g of 42% solution) was added over 1 minute. The mixture was transferred to a jacketed resin flask, and its temperature was held at 50 to 55° C. for 4 hours. Sodium nitrate (29 g) was then added to the mixture over 15 minutes. Subsequently, calcium chloride (37 g) was added to the mixture over 15 minutes. The pH of the mixture was then adjusted to approximately 7.0 by adding a sufficient amount of acetic acid. Xanthan gum (0.3 g, Kelzan S) suspended in water (81.2 g) was added to the mixture. Finally, a biocide (0.15 g, Proxel GXL) was added.

The analytical assay of clomazone of 33.5% in the composition compared favorably to the calculated value of 34%. The loading level of clomazone in the composition did not change significantly over a two-week period while kept at the room temperature. The loading level of clomazone in the composition did not change over a two week period while kept at 54° C. The mean particle size, as determined by routine testing on the Horiba Laser Scattering Particle Size Distribution Analyzer LA-950, was found to be about 13.3 micrometers.

To evaluate the freeze-thaw stability of Formulation A, a 250 mL sample of Formulation A was placed into a freezer controlled to −10° C.+/−5° C. for one day. The sample was then removed, and after allowing the sample to equilibrate to room temperature, the cycle was repeated two more times. At the end of the three freeze-thaw cycles, the sample was observed for crystal formation, particle size growth, changes in viscosity, changes in chemical composition, density, dispersion, and suspension. No substantial changes were observed in the sample, and Formulation A was thus determined to be stable to freeze-thaw cycles.

Greenhouse Ring Volatility Testing

To determine the volatility of the herbicidal composition of Formulation A relative to that of the standard, Command® 4EC, and relative to the commercially available encapsulated clomazone Command® 3ME, tests were carried out using the following Greenhouse Ring Volatility Test. For each test, a plastic 10 cm×10 cm (4 inch×4 inch) horticultural pot (Kord 4 inch Square pot Model 309) was filled with Pennington sandy loam that was sieved using a #10 mesh sieve to remove any large particles and debris. The soil was left barren and sprayed with DeVries Generation III sprayer at a rate of 280 L/ha (30 gal/acre) to deliver 0.25 kg/ha (0.22 lb/acre) of the active ingredient clomazone. The treated soil pot was placed in a greenhouse and linear arrays of 7.5×7.5 cm (3 inch×3 inch) pots containing 18-day old, approximately 5 cm (2 inches) tall, chickweed grown in MetroMix planting media were placed in each of the four compass directions. The volatility was evaluated at 5 days after treatment ("DAT") and at 10 DAT by measuring the linear distance from the center of the treated soil pot to the distal point where the clomazone bleaching effects are observed in each of the four arrays. The ratio of the linear distance to the distal point where the clomazone bleaching effects are observed to the linear distance of the linear array (approximately 40 cm) is listed in the following table.

| Composition | Array 1 | Array 2 | Array 3 | Array 4 | Average | Std. Dev. |
|---|---|---|---|---|---|---|
| 5 days after formulation introduction | | | | | | |
| Untreated | 0 | 0 | 0 | 0 | 0 | |
| Command 4EC | 98% | 100% | 95% | 100% | 98% | 2.2% |
| Command 3ME | 45% | 33% | 30% | 44% | 38% | 7.5% |
| Formulation A | 48% | 20% | 26% | 29% | 31% | 11.9% |
| 10 days after formulation introduction | | | | | | |
| Untreated | 0 | 0 | 0 | 0 | 0 | |
| Command 4EC | 100% | 100% | 100% | 100% | 100% | 0% |
| Command 3ME | 48% | 53% | 70% | 66% | 59% | 10.6% |
| Formulation A | 49% | 33% | 50% | 53% | 46% | 9.3% |

The above table shows that the Command® 4EC, the commercial herbicide containing 48 weight percent of non-encapsulated emulsifiable concentrate of clomazone, causes injury to almost all of the plants in the tested area 5 days after its introduction to the center of the tray, and all of the plants 10 days after its introduction. This is indicative of high volatility of Command® 4EC.

The table above also demonstrates that the commercially available microencapsulated form of clomazone, Command® 3ME, causes on average an injury on plants 38% or less of the distance from the release point to the edge of the tray after 5 days, and causes on average an injury on plants 59% or less of the distance from the release point to the edge of the tray after 10 days. This indicates that compared to the Command® 4EC, the microencapsulated form of clomazone is effective in reducing the volatility of clomazone. The fact that the injury increases with time also suggests that encapsulated formulation is controlled release formulation, meaning that it continuously releases the active ingredient clomazone.

The table above also shows that Formulation A, the encapsulated form of clomazone and linseed oil solution, causes on average an injury on plants 31% or less of the distance from the release point to the edge of the tray after 5 days, and causes on average an injury on plants 46% or less of the distance from the release point to the edge of the tray after 10 days. This indicates that compared to the Command® 4EC, the microencapsulated form of clomazone is effective in reducing the volatility of clomazone. It is surprising and unexpected that the encapsulated solution of clomazone and linseed oil has a much lower volatility rate than the commercially encapsulated form of clomazone Command® 3ME. The fact that the injury increases with time also suggests that encapsulated formulation is a controlled release formulation, meaning that it continuously releases the active ingredient clomazone.

The volatility effect on the chickweed was also determined by using the extent of the injuries on chickweed in each array to calculate an area that is affected by the volatility of clomazone. The areas of chickweed field affected by volatilities of Formulation A and Command® 3ME were normalized with respect to the area affected by Command® 4EC, and is presented in the table below. A volatility effect of less than 50% is preferred. More preferred are compositions with volatility effect of less than 25%.

| Composition | 5DAT volatility effect | 10DAT volatility effect |
|---|---|---|
| Command ® 4EC | 100% | 100% |
| Command ® 3ME | 13% | 38% |
| Formulation A | 6% | 19% |

The data of this table show that the microencapsulated clomazone-linseed oil composition of Formulation A is of much lower volatility than the non-encapsulated clomazone-based commercial herbicide Command® 4EC. This result is indicative that the off-site injury to beneficial plants is dramatically lower than as for Command® 4EC.

More importantly, and quite unexpectedly, the clomazone-linseed oil composition of Formulation A showed a lower volatility effect than the currently available microencapsulated Command® 3ME. It is surprising that the volatility of the clomazone-linseed oil composition of Formulation A was only about half that of the currently available microencapsulated Command® 3ME. There are no suggestions in the prior art that there would be such a lowering of volatility effect.

Greenhouse Study

Seeds of barnyard grass (*Echinochloa crus-galli*), green foxtail (*Setaria viridis*), and velvetleaf (*Abutilon theophrasti*), all of which are weeds that are known to be susceptible at various levels to clomazone, and seeds of agriculturally important and beneficial plant oilseed rape (*Brassica napus*) which is considered to be a non-targeted species, were planted in a 25 cm×15 cm×7.5 cm fiber flat containing topsoil. Each species was planted as a single row in the flat, which contained five rows. There were four replicate flats of plants for each rate of application of test formulation. Stock dispersion of Formulation A was prepared by dispersing a sufficient amount of formulation to provide 0.0356 gram of active ingredient in 40 mL of water. From the stock dispersion 20 mL was removed and serially diluted with 20 mL of water to provide application rates of 0.25, 0.125, 0.0625, 0.0313, 0.0156, and 0.0078 kg of clomazone per hectare. The dispersions of test formulation for each rate of application were then sprayed onto the surface of the soil by a track-sprayer in a spray hood. Flats were also sprayed as above with the same rates of the standard Command® 4EC herbicide, and Command® 3ME herbicide. Untreated controls were also included in each test. Upon completion of the spraying the flats were placed in a greenhouse, where they were maintained for fourteen days. After this time the test was visually evaluated for percent weed control.

The comparison of the results of the weed control, across different species and loading levels for the emulsifiable clomazone-based Command® 4EC, commercially available microencapsulated clomazone based Command® 3ME, and Formulation A as prepared in Example 1, is presented in the following table.

| Formulation | Rate (kg ai/ha) | Oilseed Rape | Barnyard Grass | Green Foxtail | Velvetleaf |
|---|---|---|---|---|---|
| Command 4EC | 0.25 | 57 | 100 | 100 | 100 |
| Command 4EC | 0.125 | 33 | 100 | 95 | 100 |
| Command 4EC | 0.0625 | 16 | 93 | 79 | 100 |
| Command 4EC | 0.0313 | 7 | 83 | 43 | 83 |
| Command 4EC | 0.0156 | 1 | 62 | 30 | 82 |
| Command 4EC | 0.0078 | 0 | 23 | 16 | 61 |
| Command 3ME | 0.25 | 35 | 97 | 92 | 100 |
| Command 3ME | 0.125 | 14 | 92 | 73 | 99 |
| Command 3ME | 0.0625 | 7 | 78 | 57 | 72 |
| Command 3ME | 0.0313 | 1 | 57 | 30 | 72 |
| Command 3ME | 0.0156 | 0 | 37 | 16 | 61 |
| Command 3ME | 0.0078 | 0 | 9 | 5 | 53 |
| Formulation A | 0.25 | 30 | 100 | 89 | 98 |
| Formulation A | 0.125 | 17 | 95 | 69 | 99 |
| Formulation A | 0.0625 | 5 | 77 | 37 | 81 |
| Formulation A | 0.0313 | 1 | 36 | 22 | 62 |
| Formulation A | 0.0156 | 0 | 11 | 6 | 29 |
| Formulation A | 0.0078 | 0 | 9 | 8 | 41 |

This table shows that under these conditions of this study, Command® 4EC, which is the commercial herbicide containing 48% by weight of non-encapsulated emulsifiable concentrate of clomazone, controls weeds (barnyard grass, green foxtail, and velvetleaf) effectively. However, Command® 4EC also has injurious properties toward non-targeted agriculturally important and beneficial plants, as illustrated by the high values of injuries to oilseed rape.

The table above also demonstrates that the commercially available microencapsulated form of clomazone, Command® 3ME, controls weeds on almost the same levels as Command® 4EC, but Command® 3ME has a much lower rate of injuring the non-targeted plant.

The above table also shows that Formulation A is effective in causing injuries to the weeds on comparable levels as Command® 4EC, but it has a much lower rate of injuring the non-targeted plant.

It is surprising and unexpected that the injuries to the non-targeted beneficial plant oilseed rape were slightly lower when Formulation A was applied than when the commercial encapsulated clomazone product Command® 3ME was applied.

Example 2

Development of High Loading Clomazone Microencapsulated Composition

An herbicidal composition comprising microencapsulated clomazone wherein the clomazone content is significantly higher than the content of the commercially available microencapsulated clomazone is illustrated by Formulation B.

Preparation of Clomazone-Linseed Oil-Ammonium Sulfate Composition (Formulation B)

Technical grade clomazone (452 g, 94.8% pure), corn oil (17.6 g), and polymethylene polyphenylisocyanate (55.9 g PAPI® 27, Dow Chemical Company) were added to a beaker to yield an organic mixture. In a separate stainless steel blender cup, sodium lignosulfonate (12.8 g Reax 88B, MeadWestvaco Corporation) was stirred vigorously with water (360 g) at high speed on a blender (Waring Commercial Blender, Model HGBSSSS6) to give an aqueous mixture. The temperature of both the aqueous mixture and the organic mixture was raised to 45° C. While held at that temperature, with the stirring stopped, the organic mixture was added to the aqueous mixture. After the addition was complete, the resulting mixture was mixed at high speed for 15 sec. The stirring was then reduced to a lower speed, and a 1,6-hexanediamine aqueous solution (54.7 g of 43% solution) was added over 1 minute. The mixture was transferred to a jacketed resin flask, and its temperature was held at 50° to 55° C. for 4 hours. The pH of the mixture was then adjusted to approximately 6.9 by adding a sufficient amount of glacial acetic acid. Ammonium sulfate (70.5 g) milled with xanthan gum (0.52 g, Kelzan S, CP Kelco) was added to the mixture as a powder. Finally, a biocide (0.26 g, Proxel GXL) was added.

The analytical assay of clomazone of 41.9% in the composition matches the calculated value of 41.9%. The mean particle size, as determined by routine testing on the Horiba Laser Scattering Particle Size Distribution Analyzer LA-950, was found to be about 13.9 micrometers. The room temperature viscosity was measured as 2060 cP, and the density was 1.118 g/mL.

Greenhouse Study of Formulation B

Seeds of barnyardgrass (*Echinochloa crus-galli*), green foxtail (*Setaria viridis*), shattercane (*Sorghum bicolor*), and velvetleaf (*Abutilon theophrasti*), all of which are weeds that are known to be susceptible at various levels to clomazone, and seeds of the agriculturally important and beneficial plant oilseed rape (*Brassica napus*), which is considered to be a non-targeted species, were planted, and treated in a similar fashion as in Example 1, except that Formulation B was used in place of Formulation A.

The comparison of the results of weed control, across different species and loading levels for the emulsifiable clomazone-based Command® 4EC, commercially available microencapsulated clomazone-based Command® 3ME, and Formulation B as prepared in Example 2, is presented in the following table.

| FORMULATION | Rate (kg a.i./ha) | Oilseed Rape | Barnyard Grass | Green Foxtail | Shattercane | Velvetleaf |
|---|---|---|---|---|---|---|
| Command 4EC | 0.25 | 36 | 100 | 100 | 83 | 100 |
| Command 4EC | 0.125 | 20 | 100 | 95 | 71 | 100 |
| Command 4EC | 0.0625 | 9 | 90 | 87 | 47 | 88 |
| Command 4EC | 0.0313 | 4 | 83 | 67 | 11 | 83 |
| Command 4EC | 0.0156 | 0 | 69 | 43 | 0 | 68 |
| Command 4EC | 0.0078 | 0 | 37 | 27 | 0 | 51 |
| Command 3ME | 0.25 | 25 | 100 | 98 | 72 | 100 |
| Command 3ME | 0.125 | 6 | 99 | 87 | 48 | 85 |
| Command 3ME | 0.0625 | 4 | 89 | 72 | 15 | 80 |
| Command 3ME | 0.0313 | 0 | 71 | 47 | 2 | 66 |
| Command 3ME | 0.0156 | 0 | 47 | 24 | 0 | 45 |
| Command 3ME | 0.0078 | 0 | 21 | 7 | 0 | 27 |
| Formulation B | 0.25 | 22 | 100 | 100 | 82 | 100 |
| Formulation B | 0.125 | 12 | 100 | 81 | 67 | 100 |
| Formulation B | 0.0625 | 6 | 97 | 69 | 21 | 82 |
| Formulation B | 0.0313 | 2 | 80 | 61 | 4 | 75 |
| Formulation B | 0.0156 | 1 | 66 | 38 | 0 | 58 |
| Formulation B | 0.0078 | 0 | 42 | 32 | 0 | 46 |

This table shows that under the conditions of this study, Command® 4EC, which is the commercial herbicide containing 48 wt % of non-encapsulated emulsifiable concentrate of clomazone, effectively controls the weeds (barnyard grass, green foxtail, shattercane and velvetleaf). However, Command® 4EC also has injurious properties toward non-targeted agriculturally important and beneficial plants, as illustrated by the sizeable values of injuries to oilseed rape. The table above also demonstrates that the commercially available microencapsulated form of clomazone, i.e., Command® 3ME, causes injuries to the weeds on almost the same levels as Command® 4EC, but Command® 3ME has a much lower rate of injuring the non-targeted plant.

The above table shows that Formulation B, the encapsulated form of clomazone and linseed oil, is as effective at controlling weeds as Command® 4EC or better, but it has a lower rate of injuring the non-targeted plant.

It is surprising and unexpected that Formulation B also shows a small, but consistent improvement in controlling at least three of the four weeds, over the commercially available microencapsulated Command® 3ME.

To compare the potency of Formulation B to the commercial encapsulated clomazone product Command® 3ME, the following statistical analysis was used. The percent weed control data for Command® 4 EC, Command® 3ME, and Formulation B were subjected to a regression analysis on the linear portion of the data (i.e., the data beyond the complete or near-complete weed control was excluded, as was data beyond the total lack of weed control), and the rate of application that would provide 85% weed control (Effective Dose 85%, or $ED_{85}$) of each of the species was ascertained. From these data the relative potencies of the microencapsulated formulations were determined by dividing the $ED_{85}$ of Command® 3ME or Formulation B by the $ED_{85}$ of Command® 4EC. This ratio represents the relative potency of tested formulation normalized to Command® 4EC, where a lower number indicates a more potent formulation. The comparison of relative potency of the commercially available microencapsulated clomazone Command® 3ME and relative potency of the Formulation B is shown in the table below.

| Formulation | Oilseed Rape | Barnyard grass | Green Foxtail | Shattercane | Velvetleaf |
|---|---|---|---|---|---|
| Command 4EC | 1.00 | 1.00 | 1.00 | 1.00 | 1.00 |
| Command 3ME | 1.31 | 1.21 | 1.24 | 1.31 | 1.33 |
| Formulation B | 1.57 | 1.01 | 1.37 | 1.06 | 1.27 |

The above table summarizes the relative potency of three formulations, normalized to the emulsifiable commercial herbicide Command® 4EC.

The data in the above table indicates that Command® 3ME has a lower relative potency (i.e., higher number listed in the table) compared to Command® 4EC across all plants, that is, all weeds and beneficial plants. The characteristic of being more relatively potent to weeds than to beneficial plants is known as selectivity. Because the relative potency for Command® 3ME is roughly similar for all plants, the selectivity is similar to that of Command® 4EC. There is little or no selectivity advantage of Command® 3ME over Command® 4EC.

Formulation B has a similar or somewhat higher relative potency against weeds than Command® 3ME. Specifically, for three out of the four weeds investigated, a lower concentration of active ingredient per area of Formulation B is needed than for Command® 3ME. This difference is indicative that Formulation B is more potent than Command® 3ME. In this manner Formulation B is superior to Command® 3ME.

Furthermore, it is unexpected and surprising that Formulation B improves on selectivity compared to Command® 4EC. In order to achieve similar levels of effectiveness of Command® 4EC, the dose of Formulation B needs to be at somewhat higher loading levels of active ingredient per area (additional 1% to additional 37%) than are required for Command® 4EC. However, the amount of Formulation B that would cause injury to beneficial plants is much higher (additional 57%). This shows that Formulation B has a better selectivity than Command® 4EC.

It is also unexpected and surprising that Formulation B has a better selectivity compared to Command® 3ME. As discussed above, lower amounts of active ingredient per area of Formulation B compared to Command® 3ME are sufficient to control weeds in three out of the four weeds investigated. However, the amount of active ingredient per area of Formulation B that would cause injury to the beneficial plant oilseed rape is much higher than for Command® 3ME. This shows that the selectivity of Formulation B is better than the selectivity of Command® 4EC.

The combination of (1) lower amount of active ingredient per area of Formulation B needed for weed control compared to Command® 3ME, and (2) higher amount of active ingredient per area of Formulation B needed to cause injury to beneficial plants compared to Command® 3ME, make Formulation B an unexpectedly and unforeseeably better herbicidal composition than the commercial microencapsulated form of clomazone Command® 3ME.

Example 3

Development of High Loading Clomazone Microencapsulated Composition

An herbicidal composition comprising microencapsulated clomazone wherein the clomazone content is significantly higher than the content of the commercially available microencapsulated clomazone is illustrated by Formulations C to H. Formulations C to F demonstrate working examples of herbicides with high clomazone content, while Formulations G and H disclose attempts to make even higher clomazone-content herbicides.

Preparation of Linseed Oil-Clomazone-Ammonium Sulfate Composition (Formulation C)

Technical grade clomazone (255 g, 94.8% pure), linseed oil (25.7 g), and polymethylene polyphenylisocyanate (31.7 g, PAPI® 27, Dow Chemical Company) were added to a beaker to yield an organic mixture. In a separate stainless steel blender cup, sodium lignosulfonate (7.23 g, Reax 88B, MeadWestvaco Corporation) was stirred vigorously with water (229 g) at high speed on a blender (Waring Commercial Blender, Model HGBSSSS6) to give an aqueous mixture. The temperature of both the aqueous mixture and the organic mixture was raised to 45° C. While held at that temperature, with the stirring stopped, the organic mixture was added to the aqueous mixture. After the addition was complete, the resulting mixture was mixed at a high speed for 30 sec. The stirring was then reduced to a lower speed, and a 1,6-hexanediamine aqueous solution (31.1 g of 43.0% solution) was added over 1 minute. The mixture was transferred to a jacketed resin flask, and its temperature was held at 50° to 55° C. for 4 hours. The pH of the mixture was then adjusted to approximately 7.16 by adding a sufficient amount (3.32 g) of glacial acetic acid. Ammonium sulfate (40.1 g) milled together with xanthan gum (0.30 g, Kelzan S, CP Kelco) was added to the mixture over 15 minutes. The temperature was reduced to 40° C., and the mixture was mixed for one additional hour. Finally, a biocide (0.15 g, Proxel GXL) was added.

The analytical assay of clomazone of 39.8% in the composition is close to the calculated value of 40.6%. The mean particle size was found to be about 10.6 micrometers. The room temperature viscosity was 1740 cP, and the density was 1.107 g/mL.

Preparation of Clomazone-Linseed Oil-Ammonium Sulfate Composition (Formulation D)

Technical grade clomazone (255 g, 96.8% pure), linseed oil (15.4 g), and polymethylene polyphenylisocyanate (31.8 g, PAPI® 27, Dow Chemical Company) were added to a beaker to yield an organic mixture. In a separate stainless steel blender cup, sodium lignosulfonate (7.2 g, Reax 88B, MeadWestvaco Corporation) was stirred vigorously with water (228 g) at high speed on a blender (Waring Commercial Blender, Model HGBSSSS6) to give an aqueous mixture. The temperature of both the aqueous mixture and the organic mixture was raised to 45° C. While held at that temperature, with the stirring stopped, the organic mixture was added to the aqueous mixture. After the addition was complete, the resulting mixture was mixed at high speed for 30 sec. The stirring was then reduced to a lower speed, and a 1,6-hexanediamine aqueous solution (31.3 g of 42.9% solution) was added over 1 minute. The mixture was transferred to a jacketed resin flask, and its temperature was held at 50° to 55° C. for 4 hours. The pH of the mixture was then adjusted to approximately 6.96 by adding a sufficient amount (3.55 g) of glacial acetic acid. Ammonium sulfate (40.0 g) milled together with xanthan gum (0.30 g, Kelzan S, CP Kelco) was added to the mixture over 15 minutes. The temperature was reduced to 40° C., and the mixture was mixed for one additional hour. Finally, a biocide (0.15 g, Proxel GXL) was added.

The analytical assay of clomazone of 39.8% in the composition is close to the calculated value of 40.6%. The mean particle size was found to be about 12.1 micrometers. The room temperature viscosity was 1080 cP, and the density was 1.124 g/mL.

Preparation of Linseed Oil-Clomazone-Ammonium Sulfate Composition (Formulation E)

Technical grade clomazone (285 g, 94.8% pure), linseed oil (15.1 g), and polymethylene polyphenylisocyanate (32.2 g, PAPI® 27, Dow Chemical Company) were added to a beaker to yield an organic mixture. In a separate stainless steel blender cup, sodium lignosulfonate (7.2 g, Reax 88B, MeadWestvaco Corporation) was stirred vigorously with water (228 g) at a high speed on a blender (Waring Commercial Blender, Model HGBSSSS6) to give an aqueous mixture. The temperature of both the aqueous mixture and the organic mixture was raised to 45° C. While held at that temperature, with the stirring stopped, the organic mixture was added to the aqueous mixture. After the addition was complete, the resulting mixture was mixed at high speed for 30 sec. The stirring was then reduced to a lower speed, and a 1,6-hexanediamine aqueous solution (31.1 g of 42.8% solution) was added over 1 minute. The mixture was transferred to a jacketed resin flask, and its temperature was held at 50° to 55° C. for 4 hours. The pH of the mixture was then adjusted to approximately 7.04 by adding a sufficient amount (3.42 g) of glacial acetic acid. Ammonium sulfate (40.0 g) milled together with xanthan gum (0.30 g, Kelzan S, CP Kelco) was added to the mixture over 15 minutes. The temperature was reduced to 40° C., and the mixture was mixed for one additional hour. Finally, a biocide (0.15 g, Proxel GXL) was added.

The analytical assay of clomazone of 42.2% in the composition is somewhat lower than the calculated value of 44.0%. The mean particle size was found to be about 11.53 micrometers. The room temperature viscosity was 2720 cP, and the density was 1.129 g/mL.

Preparation of Clomazone-Linseed Oil-Ammonium Sulfate Composition (Formulation F)

Technical grade clomazone (255 g, 94.8% pure), linseed oil (10.0 g), and polymethylene polyphenylisocyanate (31.5 g, PAPI® 27, Dow Chemical Company) were added to a beaker to yield an organic mixture. In a separate stainless steel blender cup, sodium lignosulfonate (7.2 g, Reax 88B, MeadWestvaco Corporation) was stirred vigorously with water (204 g) at a high speed on a blender (Waring Commercial Blender, Model HGBSSSS6) to give an aqueous mixture. The temperature of both the aqueous mixture and the organic mixture was raised to 45° C. While held at that temperature, with the stirring stopped, the organic mixture was added to the aqueous mixture. After the addition was complete, the resulting mixture was mixed at high speed for 30 sec. The stirring was then reduced to a lower speed, and a 1,6-hexanediamine aqueous solution (31.0 g of 42.9% solution) was added over 1 minute. The mixture was transferred to a jacketed resin flask, and its temperature was held at 50° to 55° C. for 4 hours. The pH of the mixture was then adjusted to approximately 6.86 by adding a sufficient amount (3.11 g) of glacial acetic acid. Ammonium sulfate (40.0 g) milled together with xanthan gum (0.30 g, Kelzan S, CP Kelco) was added to the mixture over 15 minutes. The temperature was reduced to 40° C., and the mixture was mixed for one additional hour. Finally, a biocide (0.15 g, Proxel GXL) was added.

The analytical assay of clomazone of 40.2% in the composition is somewhat lower than the calculated value of 43.3%. The mean particle size was found to be about 13.6 micrometers. The room temperature viscosity was 2860 cP, and the density was 1.121 g/mL.

Attempted Preparation of a Very High Loading Clomazone Composition (Formulation G)

Technical grade clomazone (255 g, 94.8% pure), linseed oil (5.03 g), and polymethylene polyphenylisocyanate (31.6 g, PAPI® 27, Dow Chemical Company) were added to a beaker to yield an organic mixture. In a separate stainless steel blender cup, sodium lignosulfonate (7.2 g, Reax 88B, MeadWestvaco Corporation) was stirred vigorously with water (207 g) at a high speed on a blender (Waring Commercial Blender, Model HGBSSSS6) to give an aqueous mixture. The temperature of both the aqueous mixture and the organic mixture was raised to 45° C. While held at that temperature, with the stirring stopped, the organic mixture was added to the aqueous mixture. After the addition was complete, the base mixture was mixed at high speed for 30 sec. The stirring was then reduced to a lower speed, and a 70% 1,6-hexanediamine aqueous solution was added to the mixture, in a similar way as in Formulations A to F. By the time approximately 10 g of the 1,6-hexanediamine solution was added, the mixture gelled up very quickly, rendering the solution mixture not suitable for further use.

Attempted Preparation of a Very High Loading Clomazone Composition (Formulation H)

Technical grade clomazone (255 g, 94.8% pure), linseed oil (5.03 g), and polymethylene polyphenylisocyanate (33.2 g, PAPI® 27, Dow Chemical Company) were added to a beaker to yield an organic mixture. In a separate stainless steel blender cup, sodium lignosulfonate (7.2 g, Reax 88B, MeadWestvaco Corporation) was stirred vigorously with water (229 g) at a high speed on a blender (Waring Commercial Blender, Model HGBSSSS6) to give an aqueous mixture. The temperature of both the aqueous mixture and the organic mixture was raised to 45° C. While held at that temperature, with the stirring stopped, the organic mixture was added to the aqueous mixture. After the addition was complete, the base mixture was mixed at high speed for 30 sec. The stirring was then reduced to a lower speed, and a 70% 1,6-hexanediamine aqueous solution was added to the mixture, in a similar way as in Formulations A to F. By the time 7.41 g of the 1,6-hexanediamine solution was added, the mixture gelled up very quickly, rendering the solution mixture not suitable for further use.

The analytical results of Formulations C to F show that it is possible to synthesize microencapsulated formulations with loading levels of up to 44% by weight clomazone. For each of the formulations, the clomazone loading levels measured between 37.6% and 44.0% by weight.

Greenhouse Study

Seeds of barnyard grass (*Echinochloa crus-galli*), green foxtail (*Setaria viridis*), shattercane (*Sorghum bicolor*), and velvetleaf (*Abutilon theophrasti*), all of which are weeds that are known to be susceptible at various levels to clomazone, and seeds of the agriculturally important and beneficial plant oilseed rape (*Brassica napus*) which is considered to be a non-targeted species, were planted, and treated in a similar fashion as in Example 1, except that Formulations C through F were used in place of Formulation A.

The comparison of the results of the weed control, across different species and loading levels for the commercially available emulsifiable clomazone-based Command® 4EC, commercially available microencapsulated clomazone-based Command® 3ME, and Formulations C to F as prepared in Example 3, is presented in the following table.

| Formulation | wt % of technical clomazone used in encapsulated material | Calculated wt % of pure clomazone in encapsulated material | Assayed wt % of clomazone in herbicidal formulation |
| --- | --- | --- | --- |
| A | 85.0 | 80.6 | 33.5 |
| B | 96.2 | 91.2 | 41.9 |
| C | 91.1 | 86.3 | 39.8 |
| D | 94.4 | 91.4 | 39.8 |
| E | 95.0 | 90.1 | 42.2 |
| F | 96.2 | 91.2 | 40.2 |
| G | 98.1 (failed) | 93.0 | — |
| H | 98.1 (failed) | 93.0 | — |

The above table demonstrates that it is possible to prepare formulations with at least up to 96.2 weight percent of clomazone in the encapsulated material. Further, the above

| Formulation | Rate (kg a.i./ha) | Oilseed Rape | Barnyard Grass | Shattercane | Green Foxtail | Velvetleaf |
| --- | --- | --- | --- | --- | --- | --- |
| Command 4EC | 0.25 | 33 | 100 | 99 | 100 | 100 |
| Command 4EC | 0.0625 | 20 | 99 | 66 | 85 | 100 |
| Command 4EC | 0.0156 | 0 | 62 | 12 | 35 | 82 |
| Command 3ME | 0.25 | 25 | 100 | 87 | 95 | 100 |
| Command 3ME | 0.0625 | 15 | 80 | 22 | 65 | 95 |
| Command 3ME | 0.0156 | 1 | 30 | 1 | 22 | 51 |
| Formulation C | 0.25 | 28 | 100 | 92 | 95 | 100 |
| Formulation C | 0.0625 | 15 | 94 | 43 | 68 | 86 |
| Formulation C | 0.0156 | 1 | 43 | 0 | 22 | 55 |
| Formulation D | 0.25 | 36 | 100 | 95 | 100 | 100 |
| Formulation D | 0.0625 | 19 | 92 | 50 | 74 | 97 |
| Formulation D | 0.0156 | 1 | 54 | 1 | 32 | 80 |
| Formulation E | 0.25 | 29 | 100 | 91 | 97 | 100 |
| Formulation E | 0.0625 | 18 | 90 | 48 | 70 | 87 |
| Formulation E | 0.0156 | 1 | 37 | 3 | 24 | 58 |
| Formulation F | 0.25 | 32 | 100 | 87 | 99 | 100 |
| Formulation F | 0.0625 | 5 | 95 | 40 | 78 | 96 |
| Formulation F | 0.0156 | 0 | 48 | 2 | 30 | 64 |

This table shows that under the conditions of this study, all of the formulations prepared are viable alternatives to the Command® 3ME. Every single Formulation C to F is superior to Command® 3ME in that it has a significantly higher loading level of clomazone in the herbicide (about 30% higher loading level over Command® 3ME), which is envisioned to translate into lower use of the herbicidal composition, leading to lower production cost, packaging costs, transportation costs, storage costs, and other costs associated with producing, handling, storing, and using liquid herbicides.

For each of the above Formulations A to F, the organic phase consists of clomazone, polymethylene polyphenylisocyanate, and linseed oil. Upon dispersion of the organic phase in aqueous phase to form an emulsion, the diamine reacts with the polymethylene polyphenylisocyanate to form a plurality of microcapsules, each comprising a polyurea shell, encapsulating droplets of the organic phase. The organic phase encapsulated by the polyurea is presumed to consist of clomazone and linseed oil only. The weight percentage of clomazone in encapsulated material (i.e., the weight of clomazone divided by the sum of clomazone and linseed oil) is listed in the table below.

The table below also shows the weight percentage of clomazone in the entire herbicidal composition as prepared according to the above procedures, as determined by assaying the herbicidal formulation.

table also shows that it is possible to prepare formulations with at least up to 44.0 weight percent of clomazone in the herbicidal formulation.

The above table also demonstrates that it is possible to prepare formulations with at least up to 91.2 weight percent of pure clomazone in the encapsulated material. In order to increase the weight percentage of pure clomazone in the encapsulated material, higher purity clomazone is needed. For example, the weight percent of pure clomazone in encapsulated material may be increased to 96.2% in Formulation F by using 99%+ pure clomazone starting material.

Example 4

Preparation of Powdered Microencapsulated Clomazone (Formulation I)

A beaker containing a mixture of high-purity clomazone (96% purity, 191.25 g) and corn oil (33.75 g) was heated up to 45° C., and polymethylene polyphenylisocyanate (23.63 g, PAPI® 27, Dow Chemical Company) was added, to yield an organic solution. In a separate stainless steel blender cup, sodium lignosulfonate (3.00 g, Reax 88B, MeadWestvaco Corporation) was stirred vigorously with water (9.15 g) at high speed on a blender (Waring Commercial Blender, Model HGBSSSS6) to give an aqueous mixture. The temperature of both the aqueous mixture and the organic solution was raised to 45° C. While held at that temperature, with the stirring stopped, the organic solution was added to the aqueous mixture. After the addition was complete, the resulting mixture was mixed at high speed for 15 sec. The stirring was then reduced to a lower speed, and a 1,6-hexanediamine aqueous solution (23.04 g of 42.6% solution) was added over 1 minute. The mixture was transferred to a jacketed resin flask, its temperature was held at 50° to 55° C. for 150 minutes, and then cooled to 25° C. After 12 hours at 25° C., the pH of the mixture was then adjusted to approximately 7.0 by adding a sufficient amount (7.50 g) of glacial acetic acid. Partially hydrolyzed polyvinyl alcohol (38.33 g, Celvol® 203, Celanese) was added to the mixture, followed by 383 g of deionized water to thin out the mixture. The resulting mixture was spray dried by using a Büchi Mini Spray Dryer in an open mode, and the resulting powder was collected.

The analytical assay of clomazone of 61.8% in the resulting powder compares favorably with calculated value of 62.9%. The powdered microencapsulated form of herbicide of Formulation I has a loading level of about twice that of the commercial microencapsulated aqueous mixture Command® 3ME.

Example 5

Preparation of Powdered Microencapsulated Clomazone (Formulation J)

A beaker containing a mixture of high-purity clomazone (96% purity, 191.25 g) and corn oil (33.75 g) was heated up to 45° C., and polymethylene polyphenylisocyanate (30.00 g, PAPI® 27, Dow Chemical Company) was added, to yield an organic solution. In a separate stainless steel blender cup, sodium lignosulfonate (5.40 g, Reax 88B, MeadWestvaco Corporation) was stirred vigorously with water (171.00 g) at high speed on a blender (Waring Commercial Blender, Model HGBSSSS6) to give an aqueous mixture. The temperature of both the aqueous mixture and the organic solution was raised to 45° C. While held at that temperature, with the stirring stopped, the organic solution was added to the aqueous mixture. After the addition was complete, the resulting mixture was mixed at high speed for 15 sec. The stirring was then reduced to a lower speed, and a 1,6-hexanediamine aqueous solution (30.00 g of 42.0% solution) was added over 1 minute. The mixture was transferred to a jacketed resin flask, its temperature was held at 50° to 55° C. for 150 minutes, and then cooled to 25° C. After 12 hours at 25° C., the pH of the mixture was then adjusted to approximately 7.0 by adding a sufficient amount (6.75 g) of glacial acetic acid. Partially hydrolyzed polyvinyl alcohol (42.00 g, Celvol® 203, Celanese) was added to the mixture, followed by 421 g of deionized water to thin out the mixture. The resulting mixture was spray dried by using a Büchi Mini Spray Dryer in an open mode, and the resulting powder was collected.

Example 6

Attempted Preparation of Microencapsulated Clomazone with High Polyvinyl Alcohol Level A beaker containing a mixture of high-purity clomazone (96% purity, 433.5 g) and corn oil (76.5 g) was heated up to 45° C., and polymethylene polyphenylisocyanate (53.55 g, PAPI® 27, Dow Chemical Company) was added, to yield an organic solution. In a separate stainless steel blender cup, sodium lignosulfonate (12.24 g, Reax 88B, MeadWestvaco Corporation) was stirred vigorously with water (387.6 g) at high speed on a blender (Waring Commercial Blender, Model HGBSSSS6) to give an aqueous mixture. The temperature of both the aqueous mixture and the organic solution was raised to 45° C. While held at that temperature, with the stirring stopped, the organic solution was added to the aqueous mixture. After the addition was complete, the resulting mixture was mixed at high speed for 15 sec. The stirring was then reduced to a lower speed, and a 1,6-hexanediamine aqueous solution (31.0 g of 42.9% solution) was added over 1 minute. The mixture was transferred to a jacketed resin flask, its temperature was held at 50 to 55° C. for 150 minutes, and then cooled to 25° C. After 12 hours at 25° C., the pH of the mixture was then adjusted to approximately 7.0 by adding a sufficient amount (9.48 g) of glacial acetic acid. Partially hydrolyzed polyvinyl alcohol (490 g, Celvol® 203, Celanese) was added to the mixture, followed by 415 g of deionized water to thin out the mixture. The resulting mixture was mixed well, and was attempted to be spray dried at 110° C., but the spray apparatus clogged up from buildup. No solid herbicide was recoverable from the main chamber. It is hypothesized that the high loading levels of polyvinyl alcohol interfered with proper function of the spray-drying process.

Example 7

Volatility Testing of Formulations I and J

A laboratory test for the volatility of clomazone from the clomazone in Formulations A and B was carried out in the following manner. Sufficient unsterilized topsoil to conduct the test was passed twice through a 14-mesh sieve to remove large particles and debris. The fine particles were then removed through a 30-mesh sieve, leaving behind topsoil of intermediate-sized particles. This intermediate-sized topsoil, 240 grams, was spread uniformly to a thickness of about one to two millimeters over an area of about 27.9 cm×41.3 cm in a tray measuring 32.4 cm×45.7 cm×1.9 cm. The topsoil was then sprayed from an overhead track sprayer calibrated to deliver 190 liters of water per hectare (20 gal/acre). The spray mix consisted of sufficient test composition to provide 0.0712 gram of clomazone active ingredient in 20 mL of water. In this manner the test composition was applied to the soil at a rate of 1.0 kg clomazone active ingredient per hectare. Immediately after treatment, the soil was enclosed in a glass jar, where it remained briefly until used.

For each test composition, four 22 mm by 300 mm glass chromatography columns, each containing a coarse sintered glass barrier at the bottom, were connected through their bottom ends to a multi-port air manifold, which delivered equal air pressure simultaneously to a number of columns. In each of the four columns was placed 59 grams of the treated topsoil, which filled about 200 mm of the column length. In the top of each column was then placed a polyurethane foam plug designed to fit inside a 21 to 26 mm diameter tube. As soon after the soil treatment as the columns could be set up, a slow stream of air (0.75 to 1.00 liter per minute per column) from the multi-port air manifold was passed through the soil in each column, causing the volatilized clomazone to collect on the polyurethane foam plug. The time between the soil treatment and the start of the air flow was about one hour. The air flow was continued for about 18 hours.

Following the 18 hour collection period, the polyurethane foam plug from each column was placed in a 20 mL plastic syringe. The polyurethane foam plug was thoroughly extracted by drawing 15 mL of methanol into the syringe and through the plug, forcing the methanol extract into a beaker, and repeating the process several times. A 0.04 mL aliquot of the 15 mL sample was diluted with 0.96 mL of methanol and 1.0 mL of water. A 0.1 mL aliquot of this solution was analyzed for clomazone content using an enzyme-linked immunosorbent assay (ELISA), a method reported by R. V. Darger et al. (*J. Agric. Food Chem.*, 1991, 39, 813-819). The total clomazone content of the foam plug, expressed in micrograms, of each sample was recorded and compared to the clomazone content of the sample from the standard, Command® 4EC (FMC Corporation). The volatility control result was calculated by dividing the weight of clomazone in the test composition extract by the weight of clomazone in the standard composition extract, then subtracting that result from 1, and multiplying by 100%. Command® 4EC, which is the 47 wt % clomazone solution, serves as the standard to which the measured volatility control of the tested samples, including the clomazone-linseed oil formulation of Example 1, are normalized. Thus, a sample with the same level of volatility control as Command® 4EC (i.e., none) would show a volatility control test result of 0%. A sample with full volatility control would show a volatility control test result of 100%. Command® 3ME, which is the 31 wt % microencapsulated solution, is the formulation with commercially acceptable volatility control to which the microencapsulated clomazone-linseed oil formulation of Example 1 is compared.

The volatility data for the comparison of the powdered microencapsulated clomazone of Formula I is compared to the commercially available emulsified clomazone, and to the commercially available microencapsulated clomazone in the table below. A volatility control of greater than 50% is preferred. More preferred are compositions with volatility control of greater than 75%.

| Composition | Volatility (% of emulsified clomazone) |
| --- | --- |
| Command 4EC | 0% |
| Command 3ME | 76% |
| Formulation I | 78% |

The data of this table shows that the powdered microencapsulated clomazone of Formulation I is of much lower volatility than the non-encapsulated clomazone based commercial herbicide Command 4EC. The data of this table shows that the powdered microencapsulated clomazone of Formulation I is of similar volatility as the aqueous solution of microencapsulated clomazone that is currently commercially available as Command® 3 ME.

The volatility data for the comparison of the powdered microencapsulated clomazone of Formulation J is compared to the commercially available emulsified clomazone, and to the commercially available microencapsulated clomazone in the table below.

| Composition | Volatility (% of emulsified clomazone) |
| --- | --- |
| Command 4EC | 0% |
| Command 3ME | 72% |
| Formulation J | 94% |

The data of this table shows that the powdered microencapsulated clomazone of Formulation J is of much lower volatility than the non-encapsulated clomazone-based commercial herbicide Command® 4EC. The data of this table shows that the powdered microencapsulated clomazone of Formulation J is of much greater volatility control than the aqueous solution of microencapsulated clomazone that is currently commercially available as Command® 3ME.

Based on the reproducibility of the volatility test, the difference (76% vs. 72%) in the volatility of Command® 3ME when measured during the testing of volatility of Formulation I and the volatility of Command® 3ME when measured during the testing of volatility of Formulation J, is within the experimental error.

Example 9

Wettable Powder Formation (a) Aclonifen Wettable Powder:

A wettable powder formulation of aclonifen was prepared by blending 21.788 kg aclonifen technical (99.3% purity), 898 g sodium alkylbenzene sulfonate (STEPWET®DF-90), 4.531 kg sodium lignosulfonate (POLYFON® O), 2.286 kg naphthalene sulfonate condensate (AGNIQUE® NSC 3NP), 408.2 g defoamer (AGNIQUE® SOAP L), 5.455 kg ammonium sulfate and 5.455 kg Continental clay in a blender for 10 minutes. The resulting powder was milled in an air mill until a particle size of less than 15 microns was achieved, to yield 40.823 kg aclonifen wettable powder. The wettable powder was analyzed by high performance liquid chromatography (HPLC) and found to contain 53.6% aclonifen by weight with an average particle size of 10.1 micrometers (D90).

(b) Napropamide Wettable Powder:

A wettable powder formulation of napropamide was prepared by blending 7.081 kg napropamide technical (96.4% purity), 317.5 g sodium 2-[methyloleoylamino]-1-sulfonate (GEROPON® T77), 1.111 kg sodium alkylnaphthalenesulfonate (MORWET® D-425 POWDER), 793.8 g naphthalenesulfonic acid polymer with formaldehyde sodium salt (VULTAMOL® NH 7519), 7.9 g defoamer (AGNIQUE® SOAP L), 158.8 g precipitated silica (HiSil™ ABS), 3.202 kg ammonium sulfate and 3.202 kg Continental clay in a blender for 10 minutes. The resulting powder was milled in an air mill until a particle size of less than 15 microns was achieved, to yield 15.875 kg napropamide wettable powder. The wettable powder was analyzed by HPLC and found to contain 44.0% by weight napropamide with D90 of 8.76 microns.

Example 10

Encapsulated Clomazone Composition

A mixture of 392.2 grams of deionized water, 9.0 grams of lignosulfonate sodium salt (Reax® 88B) and 1.11 grams of DowCorning® Antifoam AF was added to a stainless steel beaker and the mixture was stirred and heated to 55° C. (aqueous phase).

In a separate stainless steel beaker a mixture of 300.0 grams of clomazone (96.3% purity), 42.8 grams of corn oil and 36.0 grams of methylene diphenyl diisocyanate was blended while maintaining a temperature of at least 55° C. (water-immiscible phase).

The 55° C. aqueous phase was transferred to a Waring blender equipped with a stainless steel pitcher and, while blending on a high setting, the water-immiscible phase was added. The resultant mixture was blended on a high setting for about 15 seconds then the mixing speed lowered to medium. 28.8 g hexamethylene diamine was added to the mixture and stirring was continued for 2 minutes. The mixture was transferred to a heated glass reactor and stirred for 2 hours, maintaining a temperature of 50 to 55° C., to cure the microcapsules. The cured capsule mixture was transferred to a stainless steel adjustment tank and cooled to 30° C. With stirring, 90.0 g sodium nitrate was added to the microcapsule mixture maintaining a temperature of 40° C. or less. The pH of the mixture was adjusted by the addition of 3.81 g of glacial acetic acid. A biocide, 0.18 g of Proxel™ GXL Preservative, was added. Stirring was continued until a uniform mixture was obtained. Step B was repeated four more times to provide 4.306 kg of the microcapsule composition; HPLC assay for clomazone was 33.0% by weight.

Example 10A

Encapsulated Clomazone Composition

Another preparation of encapsulated clomazone was prepared using the above procedure of Example 10 with the following changes: no sodium nitrate or Proxcel™ GXL was added; Celvol 24-203 (partially hydrogenated polyvinyl alcohol available from Celanese Corporation) 8.79% by weight of the total composition and Reax® 88B, 6.54% by weight of the total composition were added. This composition was labeled Example 10A.

Example 11

Process to Prepare Water-dispersible Granules Containing Aclonifen and Encapsulated Clomazone by Pan Pelletization 27.21 kg of aclonifen wettable powder prepared as in Example 9(a), 2.730 kilograms of the a clomazone microcapsule composition prepared as in Example 10, and 1.240 kg of deionized water were added to a Littleford plow mixer and blended until a homogenous dough was formed. The dough was fed onto a Feeco disc pelletizer set at a 50 degree angle and sprayed with an additional 2.041 kg of deionized water to form granules. The granules were dried in a fluidized bed drier at 55° C. for 15 minutes. The dry granules were screened to collect granules sized at −8 to 30 mesh (19.05 kg) with an HPLC assay of 50.0% aclonifen and 3.1% clomazone by weight. This formulation was tested for volatility, and the results are presented in Table 1 below.

Example 11A

Process to Prepare Water-Dispersible Granules Containing Aclonifen and Encapsulated Clomazone by Pan Pelletization Another preparation of water-dispersible granules prepared according to this Example was tested for stability. The results of that testing are presented in Table 1 below.

Example 12

Process to Prepare Water-Dispersible Granules Containing Napropamide and Encapsulated Clomazone by Pan Pelletization 14.968 kg of a napropamide powder as prepared in Example 9(b), 1.645 kilograms of a clomazone microcapsule composition as prepared in Example 10, and 380 g of deionized water were added to a Littleford plow mixer and blended until a homogenous dough was formed. The dough was fed onto a Feeco disc pelletizer set at a 50 degree angle and sprayed with an additional 2 kg of deionized water to form granules. The granules were dried in a fluidized bed drier at 55° C. for 15 minutes. The dry granules were screened to collect granules sized at −8 to 30 mesh (12.7 kg) with an HPLC assay of 41.2% napropamide and 3.73% clomazone by weight. This formulation was tested for volatility, and the results are presented in Table 1 below.

Example 12A

Process to Prepare Water-Dispersible Granules Containing Napropamide and Encapsulated Clomazone by Pan Pelletization Another preparation of water-dispersible granules containing napropamide and encapsulated clomazone prepared by the process of this Example was tested for stability. The results of that testing are presented in Table 1 below.

Example 13

Process to Prepare Water-Dispersible Granules Containing Napropamide and Encapsulated Clomazone by Wurster Coating 0.94 kg of a wettable powder containing napropamide, prepared in a manner similar to Example 9(b), having an HPLC assay of 42.7% was placed into a Wurster coating apparatus. The air flow was set at the minimum setting and the temperature was set at 44° C. 59.8 g of a clomazone microcapsule composition prepared in a manner similar to Example 10, having an HPLC assay of 32.6%, was sprayed onto the wettable powder during a 30 minute period. The resulting granules, 906 g, having a size of 1 mm to 3 mm, were collected. HPLC assay indicated the granules contained 40.0% napropamide and 3.5% clomazone by weight. This formulation was tested for volatility and stability. The results of that testing are presented in Table 1 below.

Example 14

Process to Prepare Water-Dispersible Granules Containing Aclonifen and Encapsulated Clomazone by Wurster Coating A wettable powder containing 0.948 kg aclonifen prepared in a manner similar to Example 9(a), having an HPLC assay of 53.4%, was placed into a Wurster coating apparatus. The air flow was set at the minimum setting and the temperature was set at 30° C. A clomazone microcapsule composition prepared in a manner similar to Example 10 having an HPLC assay of 32.6% was diluted with water until an assay of 30.0% was obtained. 51.3 g of the clomazone mixture, was sprayed onto the wettable powder during a 22-minute period. The resulting granules, 990 g, having a size of 1 mm to 3 mm, were collected. HPLC assay indicated the granules contained 50.1% aclonifen and 3.0% clomazone by weight. The formulation was tested for volatility. The results of that testing are provided in Table 1 below.

Example 15

Process to Prepare Water-Dispersible Granules Containing Aclonifen and Encapsulated Clomazone by Fluid Bed Granulation A mixture of 3.5 kilograms of aclonifen technical (99.0% purity), 139.9 g of sodium alkylbenzene sulfonate (STEPWET® DF-90), 705.9 g of sodium lignosulfonate (POLYFON® O), 356.0 g of naphthalene sulfonate condensate (AGNIQUE® NSC 3NP), 813.6 g of ammonium sulfate, 779.9 g of Continental clay and 6.86 kg of deionized water was wet milled in a Dynomill ball mill until a particle size of D90<15 micrometers was obtained. This mixture was transferred to a blender and 494.6 g of clomazone microcapsule composition, prepared in a manner similar to Example 10, was added. The mixture was stirred until homogeneous. The homogeneous mixture was fed into a fluid bed granulator having a bed temperature of 47° C., an air inlet temperature of 86° C. and an outlet temperature of 43° C., at a spray rate of 48 g/min and an air flow of 80 m$^3$/hr. The resulting granules were analyzed by HPLC to contain 51.2% aclonifen by weight and 2.78% clomazone by weight and had an average size of about 9.6 micrometers.

Example 16

Volatility Testing for Clomazone

The granules prepared in Examples 11 and 12 were tested for clomazone volatility control using the following method. Soil of a granular nature (obtained by sieving) with a typical analysis of 45% sand, 35% silt, and 20% clay, an organic matter level of 1.5% a pH of 6.0, and a moisture content of 10% to 12%, by weight was treated by spraying with the clomazone-containing formulation. The treated soil was then placed in a glass column where air passed among the soil particles. As the clomazone volatilized off the soil particles it was carried out of the soil by the air stream. The volatilized clomazone was then trapped on a foam plug at the end of the column. The clomazone was extracted from the foam with methanol following the collection period. The extract was analyzed for clomazone using HPLC, using a triple quadrupole mass detector (LC/MS/MS).

Sieved soil, 240 g of soil particles that passed through the 10 mesh sieve but did not pass through the 30 mesh sieve was spread on a 32.4 cm×45.7 cm×1.9 cm deep tray, so as to have a fairly uniform layer that was about 2 mm thick. The clomazone formulation was applied by spraying the soil surface at a rate of 0.89 lb./A, using an overhead track sprayer calibrated to deliver 30 gallons of water per acre. The spray mix consisted of 0.0712 g of active ingredient of the clomazone formulation in 20 mL of water. Immediately after treatment, the soil was transferred to a labeled glass jar, where it was mixed by rolling and shaking the jar briefly. The soil was kept in the jar for a short period (less than one hour) before it was weighed and placed in the columns.

Using filter paper cut to the dimensions of the soil on the tray, and using water in the sprayer, it was determined that an average of 3.0 mL of the spray solution was deposited on the soil from the nozzle on the track sprayer, which calculates to 2.625 micrograms of clomazone applied to each 240 g soil sample.

Treated soil (59 g) was placed into 22 mm×300 mm glass chromatography columns that contained a coarse frit at the bottom. The frit kept the soil in the column and dispersed the air stream that was coming in through the bottom of the column. This amount allowed the sample of treated soil to be split between four replicates. Polyurethane foam plugs (Identi-Plug #60882-178), designed to fit inside a 21 to 26 mm diameter tube, were inserted into the top of the chromatography column. This left a gap of about 70 mm between the top of the soil and the foam plug. One plug was used in each column. To fill the columns, treated soil was poured in through a protective paper sleeve that prevented the treated soil from contacting the sides of the column. This prevented contamination of the sample collection plug.

The air flowing into the column was humidified by bubbling it through deionized water using a fritted glass gas dispersion tube in order to decrease the rate of soil drying. Once airflow began (line pressure—2.0 lb/sq. inch), the flow through each column was measured to assure proper system function and to confirm that the variation between columns within a replicate was small. The airflow was measured again just before sample collection was terminated, to make sure there had not been any major changes. Termination of the airflow after 18 hours ended the collection of clomazone.

The foam plug was extracted by removing it from the column and placing it in a 20 cc plastic syringe. Methanol (15 ml) was drawn up in the syringe through the plug three times so as to thoroughly extract the clomazone from the foam. The methanol was squeezed from the foam into 20 ml scintillation vials, and the sample was retained for analysis. The extracted samples were diluted 1:10 prior to analysis on LC/MS/MS. Thus 100 ul of the extracted sample was added to 900 microliters of methanol.

The amount of clomazone collected from the test formulations was compared to the amount of clomazone collected from commercial formulations of clomazone tested in the same manner as the test formulations, Command® 4EC (no volatility control) and Command® 3ME (used as a standard measure), both formulations available from FMC Corporation. The % volatility control result was calculated by Commercially acceptable volatility control is considered to be about 70% control or better. Samples of the water dispersible granules were tested for initial volatility control. Samples were also tested for stability and volatility control at a) 2 months at room temperature, b) 2 weeks at 54° C. followed by 3.5 months at room temperature, and c) 1 month at 50° C. followed by 1 month at room temperature. Other samples were also tested for clomazone volatility control after similar periods of time which are indicated in the Table. The volatility data is summarized in Table 1 below:

TABLE 1

| Test Formulation | % Volatility Control Compared to 4EC Formulation |
|---|---|
| Volatility Test 1 | |
| 3ME | 91.2 |
| 4EC | 0 |
| Example 11 | 92.6 |
| Volatility Test 1A | |
| 3ME | 86.1 |
| 4EC | 0 |
| Example 11A | 87.8 |
| Example 11A; 2 weeks at 54° C.; 3.5 months room temperature | 76.6 |

TABLE 1-continued

| Test Formulation | % Volatility Control Compared to 4EC Formulation |
|---|---|
| Example 11A; 3 Months at 50° C.; 1 month room temperature | 71.1 |
| Volatility Test 2 | |
| 3ME | 87.9 |
| 4EC | 0 |
| Example 12 | 90.8 |
| Volatility Test 2A | |
| 3ME | 87.9 |
| 4EC | 0 |
| Example 12A; 2 months room temperature | 92.1 |
| Example 12A; 2 weeks at 54° C.; 3.5 months room temperature | 86.2 |
| Example 12A; 1 Months at 50° C.; 1 month room temperature | 86.8 |
| Volatility Test 3 | |
| 3ME | 85 |
| 4EC | 0 |
| Example 13 | 87 |
| Volatility Test 4 | |
| 3ME | 85 |
| 4EC | 0 |
| Example 14 | 80 |
| Example 14; 16 months room temperature | 76 |
| Volatility Test 4A | |
| Command CS | 85 |
| Comand CS; 1 week at 50° C. | 85 |
| Example 14 | 87 |
| Example 14; 1 week at 50° C. | 82 |
| Volatility Test 5 | |
| 3ME | 85.2 |
| 4EC | 0 |
| Example 19 | 87 |
| Example 19; 1 week at 50° C. | 82 |
| Volatility Test 6 | |
| Example 22 | 80.3 |
| Example 22; 2 weeks at 54° C. | 78.0 |
| Volatility Test 7 | |
| Example 22A | 75.2 |
| Example 22A; 2 weeks at 54° C. | 72.5 |
| Volatility Test 8 | |
| Example 24 | 69.5 |
| Example 24; 2 weeks at 54° C. | 63.1 |
| Example 24; 8 Month Room Temperature | 72.0 |
| Volatility Test 9 | |
| Example 24A | 72.0 |
| Example 24A; 2 weeks at 54° C. | 66.6 |

TABLE 1-continued

| Test Formulation | % Volatility Control Compared to 4EC Formulation |
|---|---|
| Example 24A; 8 Month Room Temperature | 74.0 |
| Volatility Test 10 | |
| Example 24B | 74.5 |
| Example 24B; 2 weeks at 54° C. | 69.2 |
| Volatility Test 11 | |
| Example 24C | 74.8 |
| Example 24C; 2 weeks at 54° C. | 73.5 |
| Volatility Test 12 | |
| Example 25 | 69.8 |
| Example 25; 2 weeks at 54° C. | 67.7 |
| Volatility Test 13 | |
| Example 26 | 82.8 |
| Example 26; 2 weeks at 54° C. | 73.3 |
| Volatility Test 14 | |
| Example 27 | 83.3 |
| Example 27; 2 weeks at 54° C. | 72.5 |
| Volatility Test 15 | |
| Example 28 | 83.6 |
| Example 28; 2 weeks at 54° C. | 79.8 |
| Volatility Test 16 | |
| Example 29 | 76.0 |
| Example 29; 2 weeks at 50° C. | 47 |

As can be seen from Table 1, the extrusion process described in Example 29 provides good initial volatility control of clomazone, however stability testing at 50° C. for 2 weeks indicates a breakdown of volatility control and is not a preferred process of the present invention. The processes of spray drying, Wurster coating, pan agglomeration and fluid bed granulation provide water dispersible granules of the present invention that exhibit volatility control that is commercially acceptable at both initial time and in stability testing.

Example 17

Preparation of Microencapsulated Formulation Containing Clomazone, Metolachlor, and Sulfentrazone An aqueous reaction mixture of 210.35 g tap water and 10.21 g Reax 88B bulk powder was prepared. An organic reaction mixture of 71.44 g clomazone technical (96%), 71.44 g metolachlor technical, 17.86 g sulfentrazone technical, 30.62 g aromatic SC 200, and 22.29 g polymeric isocyanate (PAPI® 27) was prepared. The aqueous and organic mixtures were heated to approximately 60° C., then combined in a stainless steel blender and agitated for 15 seconds. 22.29 g of 1,6-hexanediamine 43% (HMDA) was added over 20 seconds. The resulting emulsion was transferred to a vessel in which it was stirred at approximately 60° C. for one hour, then stirred at approximately 50° C. for twelve hours. The formulation was then neutralized with acetic acid to pH 7. The formulation was tested and found to exhibit 82.8% volatility control as compared to Command 4EC.

Example 18

Efficacy Testing of Microencapsulated Formulation Containing Clomazone, Metolachlor, and Sulfentrazone Formulations K, L, and M were prepared containing clomazone, metolachlor, and sulfentrazone with active ingredient concentrations given in the following table:

| Formulation | Clomazone | Metolachlor | Sulfentrazone |
| --- | --- | --- | --- |
| K | 9.9 | 20.0 | 4.3 |
| L | 14.8 | 14.6 | 3.6 |
| M | 13.6 | 14.0 | 3.3 |

The formulations were sprayed at various rates on test patches of Green Foxtail, Crabgrass, Velvetleaf, and Lambsquarter. On each patch, the percentage of weed control (i.e., the number of weeds prevented from growing, as measured against the control, which had no herbicide applied) was measured 14 days and 28 days after treatment. The efficacy results 14 days after treatment are provided in the following table:

| Treatment | Rate (kg/ha) | Repetition | Green Foxtail | Crabgrass | Velvetleaf | Lambsquarter |
| --- | --- | --- | --- | --- | --- | --- |
| Control | 0.0 | 1 | 0 | 0 | 0 | 0 |
| K | 0.7 | 1 | 95 | 100 | 100 | 100 |
| K | 0.35 | 1 | 85 | 75 | 100 | 100 |
| K | 0.175 | 1 | 60 | 60 | 85 | 100 |
| L | 0.9 | 1 | 98 | 100 | 100 | 100 |
| L | 0.45 | 1 | 98 | 87 | 100 | 100 |
| L | 0.225 | 1 | 65 | 40 | 100 | 100 |
| M | 0.9 | 1 | 98 | 100 | 100 | 100 |
| M | 0.45 | 1 | 75 | 100 | 100 | 100 |
| M | 0.225 | 1 | 60 | 45 | 75 | 100 |
| Control | 0.0 | 2 | 0 | 0 | 0 | 0 |
| K | 0.7 | 2 | 85 | 95 | 100 | 100 |
| K | 0.35 | 2 | 80 | 65 | 100 | 100 |
| K | 0.175 | 2 | 45 | 45 | 87 | 100 |
| L | 0.9 | 2 | 100 | 100 | 100 | 100 |
| L | 0.45 | 2 | 70 | 80 | 100 | 100 |
| L | 0.225 | 2 | 60 | 40 | 100 | 100 |
| M | 0.9 | 2 | 100 | 100 | 100 | 100 |
| M | 0.45 | 2 | 100 | 80 | 100 | 100 |
| M | 0.225 | 2 | 70 | 60 | 100 | 100 |
| Control | 0.0 | 3 | 0 | 0 | 0 | 0 |
| K | 0.7 | 3 | 100 | 100 | 100 | 100 |
| K | 0.35 | 3 | 90 | 85 | 100 | 100 |
| K | 0.175 | 3 | 60 | 55 | 98 | 100 |
| L | 0.9 | 3 | 100 | 100 | 100 | 100 |
| L | 0.45 | 3 | 100 | 98 | 100 | 100 |
| L | 0.225 | 3 | 80 | 60 | 100 | 100 |
| M | 0.9 | 3 | 100 | 100 | 100 | 100 |
| M | 0.45 | 3 | 100 | 75 | 100 | 100 |
| M | 0.225 | 3 | 70 | 50 | 100 | 100 |

The results from 28 days after treatment are provided in the following table:

| Treatment | Rate (kg/ha) | Repetition | Green Foxtail | Crabgrass | Velvetleaf | Lambsquarter |
| --- | --- | --- | --- | --- | --- | --- |
| Control | 0.0 | 1 | 0 | 0 | 0 | 0 |
| K | 0.7 | 1 | 100 | 100 | 100 | 100 |
| K | 0.35 | 1 | 80 | 60 | 100 | 100 |
| K | 0.175 | 1 | 40 | 25 | 100 | 100 |
| L | 0.9 | 1 | 100 | 100 | 100 | 100 |
| L | 0.45 | 1 | 100 | 85 | 100 | 100 |
| L | 0.225 | 1 | 60 | 40 | 100 | 100 |
| M | 0.9 | 1 | 100 | 100 | 100 | 100 |
| M | 0.45 | 1 | 75 | 100 | 100 | 100 |
| M | 0.225 | 1 | 65 | 40 | 100 | 100 |
| Control | 0.0 | 2 | 0 | 0 | 0 | 0 |
| K | 0.7 | 2 | 80 | 100 | 100 | 100 |
| K | 0.35 | 2 | 75 | 50 | 100 | 100 |
| K | 0.175 | 2 | 20 | 0 | 100 | 100 |
| L | 0.9 | 2 | 100 | 100 | 100 | 100 |
| L | 0.45 | 2 | 75 | 100 | 100 | 100 |
| L | 0.225 | 2 | 60 | 10 | 100 | 100 |
| M | 0.9 | 2 | 100 | 100 | 100 | 100 |
| M | 0.45 | 2 | 100 | 80 | 100 | 100 |
| M | 0.225 | 2 | 70 | 40 | 100 | 100 |
| Control | 0.0 | 3 | 0 | 0 | 0 | 0 |
| K | 0.7 | 3 | 100 | 100 | 100 | 100 |
| K | 0.35 | 3 | 100 | 75 | 100 | 100 |
| K | 0.175 | 3 | 40 | 30 | 100 | 100 |
| L | 0.9 | 3 | 100 | 100 | 100 | 100 |
| L | 0.45 | 3 | 100 | 80 | 100 | 100 |
| L | 0.225 | 3 | 70 | 20 | 100 | 100 |
| M | 0.9 | 3 | 100 | 100 | 100 | 100 |
| M | 0.45 | 3 | 100 | 60 | 100 | 100 |
| M | 0.225 | 3 | 60 | 35 | 100 | 100 |

Example 19

Process to Prepare Water Dispersible Granules Containing Napropamide and Encapsulated Clomazone by Spray Drying A mixture of 98.70 grams of napropamide powder (prepared as in Example 10(b)), 12.03 grams of clomazone microcapsule composition, prepared in a manner similar to Example 11, and 220.00 grams of deionized water was stirred in a 500 ml beaker until homogenous. The homogenous mixture was fed into a Buchi B290 spray drier having an inlet temperature of 110° C., at a pump speed of 15% (~6 ml minute). The resulting granules were collected in a receiver (74.0 grams) and brushed from the main chamber (20.0 grams) and combined. A sample of the granules was analyzed by HPLC to contain 40.3% napropamide by weight 3.52% clomazone by weight and had an average size of less than 25 micrometers. The results of testing for volatility control are reproduced in the table below.

|  | Example 19 | Command CS |
| --- | --- | --- |
| Initial volatility | 87 | 85 |
| 1 week @ 50° C. | 82 | 85 |

Example 20

Process to Prepare Formulation of Clomazone and Pendimethalin

An aqueous phase was prepared by combining 46.8 g Reax 88B with 1331.1 g deionized water and warming to 50° C. In a separate vessel, an organic phase was prepared by combining 87.1 g clomazone technical, 954.2 g pendimethalin technical, and 122.8 g corn oil, and warming to 50°

C. Linseed oil may be substituted for corn oil at this step. 46.8 g PAPI 27 was added to the organic phase and mixed for 2-3 minutes using an overhead stirrer, then the aquous phase was charged to a blender and the organic phase was added over about 10 seconds with vigorous mixing. 52.1 g 43% HMDA, was added and mixed for 1-2 minutes. The resulting emulsion was then transferred to a curing tank. The emulsion may be produced in a single batch or the amounts listed above may be divided and the emulsion produced in multiple batches, then combined in the curing tank.

All batches were combined in the curing tank and agitated for two hours at 50° C. The emulsion was cooled to room temperature and filtered through a 60 mesh screen. 149.8 g sodium nitrate was added and dissolved. 140.4 g calcium chloride was added and dissolved. 2.5 g glacial acetic acid was added to adjust the pH to between 6.5 and 7.5. 187.3 g 1% Kelzan S/0.33% Proxel solution was added. The resultant formulation was mixed until the Kelzan was well-mixed and hydrated, a minimum of two hours.

The formulation was tested for volatility control; the results are in the following table:

|  | Example 20 | Command 3ME |
|---|---|---|
| Initial | 91 | 81 |
| 2 weeks @ 50° C. | 91 | 81 |
| 2 months @ 50° C. | 94 | 84 |

Example 21

Process to Prepare Formulation of Clomazone, Metazachlor, and Napropamide

An aqueous phase was prepared by combining 10 g Reax 88B with 473.9 g deionized water and warming to 70° C. In a separate vessel, an organic phase was prepared by combining 22.8 g clomazone technical (96.3%), 139.8 g metazachlor (98%), 141.4 g napropamide, and 70 g Aromatic 200ND. The metazachlor was melted by placing the organic phase into a 75° C., but may be melted at an oven temperature of up to 80° C. After melting, the organic phase was held at 70° C. PAPI 27, 18 g was added to the organic phase and mixed for 2-3 minutes using an overhead stirrer, then the aquous phase was charged to a blender and the organic phase was added over about 10 seconds with vigorous mixing. The organic phase should not be below 70° C. before mixing with the aqueous phase. 43% HMDA, 15 g, was added and mixed for 1-2 minutes. The resulting emulsion was then transferred to a curing tank. The emulsion may be produced in a single batch or the amounts listed above may be divided and the emulsion produced in multiple batches, then combined in the curing tank.

All batches were combined in the curing tank and agitated for seven hours at 60° C. The emulsion was cooled to room temperature and filtered through a 60 mesh screen. 30 g sodium nitrate was added and dissolved. 30 g calcium chloride anhydrous was added and dissolved. 1 g glacial acetic acid, was added to adjust the pH to not more than 7.5. 15 g 1% Kelzan S/0.33% Proxel solution was added. The resultant formulation was mixed until the Kelzan was well-mixed and hydrated, a minimum of four hours.

The formulation was tested for volatility control; the results are in the following table:

| Volatility | Example 21 | 3ME |
|---|---|---|
| Initial | 88.40% | 86.80% |
| 6 weeks @ 50° C. | 89.40% | 86.60% |

| Volatility | Example 21 (repeat) | 3ME |
|---|---|---|
| Initial | 92.19% | 88.40% |
| 3 months @ 50° C. | 92.70% | 92.40% |

Example 22

Process to Prepare Formulation of Clomazone and Metazachlor

An aqueous phase was prepared by combining 10 g Reax 88B with 460.3 g deionized water and warming to 60-70° C. In a separate vessel, an organic phase was prepared by combining 37.7 g clomazone technical, 280.6 g metazachlor, and 75.5 g Aromatic 200ND, and warming to 60-70° C. 18 g PAPI 27 was added to the organic phase and mixed for 2-3 minutes using an overhead stirrer, then the aquous phase was charged to a blender and the organic phase was added over about 10 seconds with vigorous mixing. Emulsification continued until particle size (D90) was less than 15 microns, about 1-5 minutes. 15 g 43% HMDA was then mixed in.

The emulsion was transferred to a curing tank and agitated for two hours at 50° C. The emulsion was cooled to room temperature and filtered through a 60 mesh screen. 28.6 g sodium nitrate was added and dissolved. 28.6 g calcium chloride was added and dissolved. 2.5 g glacial acetic acid was added to adjust the pH to between 6.5 and 7.5. 14.3 g 2% Kelzan S solution was added. The resultant formulation was mixed until the Kelzan was well-mixed and hydrated, a minimum of one hours.

The formulation was tested for volatility control; the results are in the following table:

| Volatility | Example 22 | 3ME |
|---|---|---|
| Initial | 91.20% | 85.20% |
| 2 wks 54 C. | 90.20% | 83.70% |
| 3 M 50 C. | 96.70% | 92.40% |

Example 22

Process to Prepare Water Dispersible Granules Containing Encapsulated Clomazone and Napropamide by Fluid Bed Granulation A napropamide mixture was prepared by combining 174.0 g of napropamide (96.7% purity), 28.0 g of Polyfon® O, 8.0 g of Supragil® WP (Sodium Isopropyl Naphtalene Sulfonate available from Rhodia), 4.0 g of Reax 88B, 20.0 grams of sodium triphosphate and 318 g water were mixed and milled to a D90 of 20 microns. Using a fluid bed granulation apparatus, 55.0 grams of sodium bicarbonate was fluidized with an air inlet temperature of 40° C. 277.0 grams of the napropamide mixture was sprayed onto the sodium bicarbonate at 18 mL/min and 1 bar atomizing pressure. Thereafter, 24.0 g of clomazone microcapsule composition, prepared in a manner similar to Example 10 was sprayed onto the granules using the same conditions as above. The micro granules were further dried in the fluid bed granulator at 60° C. for 15 minutes. The formulation was tested for volatility. The results of that testing are provided in Table 1 above.

Example 22A

Process to Prepare Water Dispersible Granules Containing Encapsulated Clomazone and Napropamide by Fluid Bed Granulation In a manner similar to the above, another napropamide mixture was prepared by combining 174.0 g of napropamide (96.7% purity), 28.0 g of Polyfon® O, 8.0 g of Supragil® WP (Sodium Isopropyl Naphtalene Sulfonate available from Rhodia), 4.0 g of Reax 88B, 20.0 g of sodium triphosphate and 318 g water were mixed and milled to D90 of 20 microns. Using a fluid bed granulation apparatus 55.0 grams of sodium bicarbonate was fluidized with an air inlet temperature of 40° C. 24.0 g of clomazone microcapsule composition, prepared in a manner similar to Example 10 was sprayed onto the sodium bicarbonate at 18 ml/min and 1 bar atomizing pressure followed by 277.0 grams of the napropamide mixture. The micro granules were further dried in the fluid bed granulator at 60° C. for 15 minutes. The formulation was tested for volatility. The results of that testing are provided in Table 1 above.

Example 23

Process to Prepare Water Dispersible Granules Containing Encapsulated Clomazone and Sulfentrazone by Fluid Bed Granulation A napropamide mixture was prepared by combining 174.0 g of napropamide (96.7% purity), 28.0 g of Polyfon® O, 8.0 g of Supragil® WP (Sodium Isopropyl Naphtalene Sulfonate available from Rhodia), 4.0 g of Reax 88B, 20.0 grams of sodium triphosphate and 318 g water were mixed and milled to a D90 of 20 microns. Using a fluid bed granulation apparatus, 55.0 grams of sodium bicarbonate was fluidized with an air inlet temperature of 40° C. 277.0 grams of the napropamide mixture was sprayed onto the sodium bicarbonate at 18 mL/min and 1 bar atomizing pressure. Thereafter, 24.0 g of clomazone microcapsule composition, prepared in a manner similar to Example 10 was sprayed onto the granules using the same conditions as above. The micro granules were further dried in the fluid bed granulator at 60° C. for 15 minutes.

Example 24

Process to Prepare Water Dispersible Granules Containing Encapsulated Clomazone and Sulfentrazone by Fluid Bed Granulation A sulfentrazone mixture was prepared by combining 84.0 g sulfentrazone (92.4% purity), 10.0 g Polyfon®F, 2.0 g Polyfon® H, 4.0 g Surpragil® WP, and 96.0 g sodium bicarbonate. This mixture was fluidized with an air inlet temperature of 40° C. The fluidized particles were sprayed with a solution of 15 g Norlig®A dissolved in 45 g water at 20 mL/min, 1 bar atomizing pressure. 380.0 g of clomazone microcapsule composition, prepared in a manner similar to Example 10A was sprayed onto the particles at 20 mL/min, 1 bar atomizing pressure. The micro granules were further dried in the fluid bed granulator at 60° C. for 15 minutes. The formulation was tested for volatility. The results of that testing are provided in Table 1 above.

Example 24A

Process to Prepare Water Dispersible Granules Containing Encapsulated Clomazone and Sulfentrazone by Fluid Bed Granulation Another sulfentrazone mixture was prepared by combining 78.6 g sulfentrazone (92.4% purity), 15.0 g Polyfon®F, 3.0 g Polyfon® H, 6.0 g Surpragil® WP, and 15.0 g attaclay and 64.0 g sodium bicarbonate. This mixture was fluidized with an air inlet temperature of 40° C. The fluidized particles were sprayed with 400.0 g of clomazone microcapsule composition, prepared in a manner similar to Example 10A at 20 mL/min, 1 bar atomizing pressure. The micro granules were further dried in the fluid bed granulator at 60° C. for 15 minutes. The formulation was tested for volatility. The results of that testing are provided in Table 1 above.

Example 24B

Process to Prepare Water Dispersible Granules Containing Encapsulated Clomazone and Sulfentrazone by Fluid Bed Granulation Another sulfentrazone mixture was prepared by mixing 43.5 g of sulfentrazone (92.4% purity), 3.0 g Polyfon® O, 4.0 g Polyfon® F, 2.0 g Surpragil® WP, 1.0 g Reax 88B, 12.0 g sodium triphosphate and 73.0 g water and milling to a D90 of 20 micrometers. Sodium bicarbonate, 60.0 g, was fluidized at an air inlet temperature of 50° C. The fluidized particles were sprayed with the sulfentrazone mixture, 115.25 g, followed by spraying 260.0 g of clomazone, prepared in a manner similar to Example 10A, at 20 mL/min, 1 bar atomizing pressure. The granules were further dried in the fluid bed granulator at 60° C. for 15 minutes. The formulation was tested for volatility. The results of that testing are provided in Table 1 above.

Example 24C

Process to Prepare Water Dispersible Granules Containing Encapsulated Clomazone and Sulfentrazone by Fluid Bed Granulation Another sulfentrazone mixture was prepared by mixing 43.5 g sulfentrazone
(92.4% purity), 3.0 g Polyfon® O, 4.0 g Polyfon® F, 2.0 g Surpragil® WP, 1.0 g of Reax 88B, 8.5 g sodium hexametapolyphosphate and 53 g water and milling to a D90 of 20 micrometers. Sodium bicarbonate, 60.0 grams, was fluidized at 50° C. inlet air temperature. The fluidized particles were sprayed with the sulfentrazone mixture, 115.25 g, followed by spraying 260.0 g of clomazone, prepared in a manner similar to Example 10A, at 20 mL/min, 1 bar atomizing pressure. The granules were further dried in the fluid bed granulator at 60° C. for 15 minutes. The formulation was tested for volatility. The results of that testing are provided in Table 1 above.

Example 25

Process to Prepare Water Dispersible Granules Containing Encapsulated Clomazone, Sulfentrazone and Hexazinone by Fluid Bed Granulation A sulfentrazone/hexazinone mixture containing 62.5 g sulfentrazone (92.4% purity), 21.8 g Hexazinone (95% purity), 10.0 g Polyfon® F, 2.0 g Polyfon® H, 4.0 g Surpragil® WP, 10.0 g Attaclay LVM and sodium bicarbonate, 60.0 g, was blended until a homogenous mixture was obtained. The mixture was fluidized at 50° C. inlet air temperature, and the particles were sprayed with 260.0 g of a clomazone microcapsule composition prepared in a manner similar to Example 10A, at 20 mL/min, 1 bar atomizing pressure. The granules were further dried in the fluid bed granulator at 60° C. for 15 minutes. The formulation was tested for volatility. The results of that testing are provided in Table 1 above.

Example 26

Process to Prepare Water Dispersible Granules Containing Encapsulated Clomazone and Diuron by Fluid Bed Granulation A diuron mixture was prepared by combining 91.0 g diuron (98.0% purity), 9.0 g Polyfon®F, 2.6 g Polyfon® H, 5.2 g Surpragil® WP, 4.0 g Ufoxane® 3A (modified sodium lignosulphonate available from Borregaard LignoTech), 8.0 g attaclay, 5.0 g sodium triphosphate and 36.0 g sodium bicarbonate. This mixture was fluidized at 40° C. inlet air temperature. The fluidized particles were sprayed with 310.0 g of a clomazone microcapsule composition, prepared in a manner similar to Example 10A, at 20 ml/min, 1 bar atomizing pressure. The micro granules were further dried in the fluid bed granulator at 60° C. for 15 minutes The formulation was tested for volatility. The results of that testing are provided in Table 1 above.

Example 27

Process to Prepare Water Dispersible Granules Containing Encapsulated Clomazone, Diuron and Hexazinone by Fluid Bed Granulation A diuron/hexazinone mixture containing 91.0 g diuron (98.0% purity), 16.0 g Hexazinone (98% purity), 9.0 g Polyfon® F, 2.6 g Polyfon® H, 5.2 g Surpragil® WP, 4.0 g Ufoxane® 3A (modified sodium lignosulphonate available from Borregaard LignoTech), 8.0 g attaclay, 5.0 g sodium triphosphate and 36.0 g sodium bicarbonate was fluidized at an air inlet temperature of 50° C. The fluidized particles were sprayed with 220.0 g clomazone, prepared in a manner similar to Example 10A, at 20 mL/min, 1 bar atomizing pressure. The granules were further dried in the fluid bed granulator at 60° C. for 15 minutes. The formulation was tested for volatility. The results of that testing are provided in Table 1 above.

Example 28

Process to Prepare Water Dispersible Granules Containing Encapsulated Clomazone and 2,4-D by Fluid Bed Granulation A 2,4-D mixture was prepared by combining 110.0 g 2,4-D (98.0% purity), 5.0 g sodium triphosphate and 45.0 g sodium bicarbonate. This mixture was fluidized at an air inlet temperature of 40° C. The fluidized particles were sprayed with 350.0 g of clomazone microcapsule composition prepared in a manner similar to Example 10A, at 20 mL/min, 1 bar atomizing pressure. The micro granules were further dried in the fluid bed granulator at 60° C. for 15 minutes. The formulation was tested for volatility. The results of that testing are provided in Table 1 above.

Example 29

Process to Prepare Water Dispersible Granules Containing Encapsulated Clomazone and Napropamide by Extrusion A mixture containing 47.35 g napropamide prepared by the method of Example 9(b), 19.33 g ammonium sulfate, 19.33 g Continental clay, 3.00 g Geopron T-77, 6.00 g Morwet D-425 and 5.00 g Ufoxane 3A, was air milled to a D90 less than 15 microns. This mixture was kneaded with 10.86 g clomazone microcapsule composition prepared in a manner similar to Example 10 and a small amount of water, then extruded using 1.0 mm die. The granules were further dried at 55° C. for 30 minutes. The formulation was tested for volatility. The results of that testing are provided in Table 1 above.

Example 30

Encapsulated Clomazone, Metolachlor and Sulfentrazone Composition, 1:4:1 Ratio

A mixture of 230.0 g water, 8.5 g lignosulfonate sodium salt (Reax® 88B) was added to a stainless steel beaker and the mixture was stirred and heated to 55° C. (aqueous phase).

In a separate stainless steel beaker a mixture of 47.8 g clomazone (96.3% purity), 140.47 g metolachlor, 47.44 grams of sulfentrazone and 32.84 g methylene diphenyl diisocyanate was blended while maintaining a temperature of at least 55° C. (water-immiscible phase).

The 55° C. aqueous phase was transferred to a Waring blender equipped with a stainless steel pitcher and, while blending on a high setting, the water-immiscible phase was added. The resultant mixture was blended on a high setting for about 15 seconds then the mixing speed lowered to medium. 28.8 g of hexamethylene diamine and 60.77 g of ammonium sulfate were added to the mixture and stirring was continued for 2 minutes. The mixture was transferred to a heated glass reactor and stirred for 2 hours, maintaining a temperature of 50 to 55° C., to cure the microcapsules. The cured capsule mixture was transferred to a stainless steel adjustment tank and cooled to 30° C. With stirring, 90.0 grams of sodium nitrate was added to the microcapsule mixture maintaining a temperature of 40° C. or less. The pH of the mixture was adjusted by the addition of 13.0 grams of water and 1.22 grams of glacial acetic acid. Stirring was continued until a uniform mixture was obtained.

The volatility control measured for these capsules was 71.0%.

Example 31

Encapsulated Clomazone, Metolachlor and Sulfentrazone Composition, 1:4:1 Ratio

A mixture of 233.23 g water, 8.6 g lignosulfonate sodium salt (Reax® 88B) was added to a stainless steel beaker and the mixture was stirred and heated to 55° C. (aqueous phase).

In a separate stainless steel beaker a mixture of 47.3 g clomazone (96.3% purity), 140.93 grams of metolachlor, 47.29 g sulfentrazone, 46.37 g linseed oil and 32.9 g methylene diphenyl diisocyanate was blended while maintaining a temperature of at least 55° C. (water-immiscible phase).

The 55° C. aqueous phase was transferred to a Waring blender equipped with a stainless steel pitcher and, while blending on a high setting, the water-immiscible phase was added. The resultant mixture was blended on a high setting for about 15 seconds then the mixing speed lowered to medium. Hexamethylene diamine (28.8 grams) and 60.45 g ammonium sulfate were added to the mixture and stirring was continued for 2 minutes. The mixture was transferred to a heated glass reactor and stirred for 2 hours, maintaining a temperature of 50 to 55° C., to cure the microcapsules. The cured capsule mixture was transferred to a stainless steel adjustment tank and cooled to 30° C. With stirring, 90.0 g sodium nitrate was added to the microcapsule mixture maintaining a temperature of 40° C. or less. The pH of the mixture was adjusted by the addition of 63.0 g water and 1.42 g glacial acetic acid. Stirring was continued until a uniform mixture was obtained.

The volatility control measured for these capsules was 83.3%.

Example 32

Encapsulated Clomazone, Metolachlor and Sulfentrazone Composition, 4.5:4:1 Ratio A mixture of 309.61 g water and 7.39 g lignosulfonate sodium salt (Reax® 88B) was added to a stainless steel beaker and the mixture was stirred and heated to 55° C. (aqueous phase).

In a separate stainless steel beaker a mixture of 116.39 grams of clomazone (96.3% purity), 105.04 g S-metolachlor, 26.72 g sulfentrazone, 45.0 g Aromatic 100 and 32.99 gd methylene diphenyl diisocyanate was blended while maintaining a temperature of at least 55° C. (water-immiscible phase).

The 55° C. aqueous phase was transferred to a Waring blender equipped with a stainless steel pitcher and, while blending on a high setting, the water-immiscible phase was added. The resultant mixture was blended on a high setting for about 15 seconds then the mixing speed lowered to medium. 32.8 g hexamethylene diamine, 36.52 g sodium nitrate and 36.43 g calcium chloride were added to the mixture and stirring was continued for 2 minutes. The mixture was transferred to a heated glass reactor and stirred for 2 hours, maintaining a temperature of 50 to 55° C., to cure the microcapsules. The cured capsule mixture was transferred to a stainless steel adjustment tank and cooled to 30° C. The pH of the mixture was adjusted by the addition of 1.391 grams of glacial acetic acid. Stirring was continued until a uniform mixture was obtained.

The volatility control measured after 3 months at 50° C. for these capsules was 85.0%.

As seen from Examples 30, 31 and 32, encapsulation of clomazone along with other active ingredients provides commercially acceptable volatility control of clomazone in both initial and stability samples.

Example 33

Encapsulated Clomazone and Pendimethalin Composition, 1:11 Ratio

A mixture of 1.33 kg water and 46.8 g lignosulfonate sodium salt (Reax® 88B) was added to a stainless steel beaker and the mixture was stirred and heated to 50° C. (aqueous phase).

In a separate stainless steel beaker a mixture of 87.1 g clomazone (96.3% purity), 954.2 g pendimethalin (melted) and 122.8 g corn oil was blended while maintaining a temperature of at least 55° C. 52.1 g methylene diphenyl diisocyanate was added and stirred until a homogenous mixture was obtained (water-immiscible phase).

The 50° C. aqueous phase was transferred to a blender equipped with a stainless steel pitcher and, while blending on a high setting, the water-immiscible phase was added. The resultant mixture was blended on a high setting for about 20 seconds then the mixing speed lowered to medium. Hexamethylene diamine (52.1 g of an aqueous 43% solution) was added to the mixture stirred for 2 minutes. The mixture was transferred to a heated glass reactor and stirred for 2 hours, maintaining a temperature of 50° C., to cure the microcapsules. The cured capsule mixture was transferred to a stainless steel adjustment tank and cooled to 30° C. With stirring, 149.8 g sodium nitrate and 140.4 g calcium chloride were added to the microcapsule mixture maintaining a temperature of 40° C. or less. The pH of the mixture was adjusted by the addition of 2.5 grams of glacial acetic acid. A 1% aqueous solution of Kelzan® xanthan gum (1.33 kg) and a small amount of Proxel® XLR biocide was added and stirring was continued until a uniform mixture was obtained.

The initial volatility control measured for these capsules was 91.0%. After storage for 2 weeks at 54° C., the volatility control was 91.0%. After 2 months at 50° C., the volatility control was 94.0%.

Example 34

Encapsulated Clomazone, Metazachlor and Napropamide Composition, 1:6:6 Ratio

A mixture of 473.9 g water and 10.0 g lignosulfonate sodium salt (Reax® 88B) was added to a stainless steel beaker and the mixture was stirred and heated to 50° C. (aqueous phase).

In a separate stainless steel beaker a mixture of 22.8 g clomazone (96.3% purity), 139.8 g metazachlor (melted), 141.4 g napropamide, 70.0 g Aromatic 200 ND and 30.0 gcorn oil grams of corn oil was blended while maintaining a temperature of at least 50° C. 18.0 g methylene diphenyl diisocyanate was added to the mixture and was stirred until homogenous (water-immiscible phase).

The 50° C. aqueous phase was transferred to a Waring blender equipped with a stainless steel pitcher and, while blending on a high setting, the water-immiscible phase was added. The resultant mixture was blended on a high setting for about 20 seconds then the mixing speed lowered to medium. Hexamethylene diamine (15.0 g of an aqueous 43% solution) was added to the mixture stirred for 2 minutes. The mixture was transferred to a heated glass reactor and stirred for 2 hours, maintaining a temperature of 50° C., to cure the microcapsules. The cured capsule mixture was transferred to a stainless steel adjustment tank and cooled to 30° C. With stirring 30.0 g sodium nitrate and 30.0 g calcium chloride were added to the microcapsule mixture maintaining a temperature of 40° C. or less. The pH of the mixture was adjusted by the addition of 1.0 g of glacial acetic acid. A 1% aqueous solution of Kelzan® xanthan gum solution (15.0 g) and 2.0 g DowCorning® AF antifoam were added and stirring was continued until a uniform mixture was obtained.

The initial volatility control measured for these capsules was 92.2%. After storage for 3 months at 50° C., the volatility control was 92.7%.

Example 35

Encapsulated Clomazone and Metazachlor Composition, 1:7.5 Ratio

A mixture of 460.3 g water and 10.0 g lignosulfonate sodium salt (Reax® 88B) was added to a stainless steel beaker and the mixture was stirred and heated to 70° C. (aqueous phase).

In a separate stainless steel beaker a mixture of 37.7 g clomazone (96.3% purity), 280.6 g metazachlor (melted), 75.5 g Aromatic 200 ND and 30.2 g corn oil was blended while maintaining a temperature of at least 70° C. 18.0 g methylene diphenyl diisocyanate was added to the mixture and was stirred until homogenous (water-immiscible phase).

The 70° C. aqueous phase was transferred to a Waring blender equipped with a stainless steel pitcher and, while blending on a high setting, the water-immiscible phase was added. The resultant mixture was blended on a high setting for about 20 seconds then the mixing speed lowered to medium. Hexamethylene diamine (15.0 g of an aqueous 43% solution) was added to the mixture stirred for 2 minutes. The mixture was transferred to a heated glass reactor and stirred for 2 hours, maintaining a temperature of 50° C., to cure the microcapsules. The cured capsule mixture was transferred to a stainless steel adjustment tank and cooled to 30° C. With stirring 28.6 g sodium nitrate and 28.6 g calcium chloride were added to the microcapsule mixture maintaining a temperature of 40° C. or less. A 2% aqueous solution of Kelzan® xanthan gum solution (14.3 g), 0.2 g of Proxcel® GXL biocide and 1.0 g of DowCorning® AF antifoam were added and stirring was continued until a uniform mixture was obtained.

The initial volatility control measured for these capsules was 91.2%. After 2 weeks of storage at 54° C., the volatility control was 90.2%. After 3 months of storage at 50° C., the volatility control was 96.7%.

Example 36

Process to Prepare Water Dispersible Granules Containing Sulfentrazone and Encapsulated Clomazone by Fluid Bed Granulation A sulfentrazone mixture was prepared by combining 40 g sulfentrazone (91.8% purity), 8 g Polyfon®F, 1.5 g Polyfon® H, 3 g Surpragil® WP, and 38 g sodium triphosphate. A clomazone mixture was prepared by combining 200 g of a clomazone microcapsule composition prepared in a manner similar to Example 10A, 14 g sodium triphosphate, 40 g PVP K30, and 60 g Reax 88B. The sulfentrazone mixture was fluidized with an air inlet temperature of 50° C. The fluidized particles were sprayed with the clomazone mixture at 1 bar atomizing pressure. The micro granules were further dried in the fluid bed granulator at 50° C. for 20 minutes.

Example 37

Process to Prepare Water Dispersible Granules Containing Encapsulated Clomazone and Sulfentrazone by Fluid Bed Granulation A sulfentrazone mixture was prepared by combining 250 g sulfentrazone (92.4%), 43 g Polyfon® F, 9 g Polyfon® H, 18 g Surpragil® WP and 180 g sodium hexametaphosphate, then milling to a D90 of approximately 20 microns. A dry components mixture was prepared by combining 110 g of the sulfentrazone mixture with 19 g hexazinone and 70 g sodium hexametaphosphate. The dry components mixture was fluidized with an air inlet temperature of 40° C. The fluidized particles were sprayed with 170 g of a clomazone composition prepared in a manner similar to Example 10A, at 18 mL/min and 1 bar atomizing pressure. The micro granules were further dried in the fluid bed granulator at 60° C. for 10 minutes.

What is claimed is:

1. A formulation comprising multilayered particles comprising:
   a core comprising clomazone,
   a first encapsulating layer surrounding the core and comprising polyurea, and
   a second encapsulating layer surrounding the first encapsulating layer and comprising polyvinyl alcohol,
   wherein the weight ratio of the polyvinyl alcohol to clomazone is from 1:6 to 1:4, the weight ratio of polyurea to polyvinyl alcohol is from 1.5:1 to 1:1.5, and further wherein the multilayered particles contain at least 50% by weight of ciomazone.

2. An herbicidal composition comprising the formulation of claim 1 and a carrier.

3. The herbicidal composition of claim 2, wherein the herbicidal composition exhibits clomazone volatility control of at least 80%.

4. The formulation of claim 1 comprising linseed oil in the core.

5. The formulation of claim 1 comprising clomazone in the core in an amount of from about 80 wt % to about 97 wt %%.

6. A method for preparing an herbicidal composition comprising the steps of:
   a) preparing an aqueous suspension of particles comprising a core and a first encapsulating layer, wherein the core comprises clornazone and the first encapsulating layer comprises polyurea;
   b) adding a polyvinyl alcohol to the aqueous suspension; and
   c) spray drying the resulting mixture;
   wherein the weight ratio of the polyvinyl alcohol to clomazone is from 1:6 to 1:4, the weight ratio of polyurea to polyvinyl alcohol is from 1.5:1 to 1:1.5, and further wherein the multilayered particles contain at least 50% by weight of clomazone.

7. A method for making water-dispersible granules for delivering agricultural chemicals to a crop comprising the steps of:
   forming a water-dispersible powder containing at least one agriculturally active ingredient;
   milling the water-dispersible powder; and
   forming water-dispersible granules by combining the water-dispersible powder with a clomazone composition, wherein the clomazone composition comprises multilayered clomazone containing particles suspended in an aqueous solution, said multilayered clomazone containing particles comprising:
   a core comprising clomazone,
   a first encapsulating layer surrounding the core and comprising polyurea, and a second encapsulating layer surrounding the first encapsulating layer and comprising polyvinyl alcohol,
   wherein the weight ratio of the polyvinyl alcohol to clomazone is from 1:6 to 1:4, the weight ratio of polyurea to polyvinyl alcohol is from 1.5:1 to 1:1.5, and further wherein the multilayered particles contain at least 50% by weight of clomazone;
wherein the granules exhibit controlled volatility.

8. The method of claim 7, wherein the step of forming water-dispersible granules comprises:
kneading the clomazone composition into the milled water-dispersible powder to form a wetted powder,
forming granules by subjecting the wetted powder to pan pelletization, and drying the granules.

9. The method of claim 7, wherein the step of forming water-dispersible granules comprises:
kneading the milled water-dispersible powder with water to form a dough,
extruding the dough to form granules,
spray coating the granules with the clomazone composition, and
drying the coated granules.

10. The method of claim 7, wherein the step of forming water-dispersible granules comprises:
kneading the clomazone composition into the milled water-dispersible powder to form a
dough, and extruding the dough to form granules
and drying the granules.

11. The method of claim 7, wherein the step of forming water-dispersible granules comprises:
mixing the milled water dispersible powder with an aqueous encapsulated clomazone composition, and
forming granules from the mixture by fluid bed agglomeration.

12. The method of claim 7, wherein the step of forming water-dispersible granules comprises:
mixing the milled water-dispersible powder with the clomzone composition, and
spray-drying the mixture to form granules.

13. The method of claim 7, wherein the step of forming water-dispersible granules comprises:
mixing the milled water-dispersible powder with the clomzone composition, and
spray-coating the mixture onto an inert carrier material.

14. The method of claim 7, wherein the agriculturally active agent is an herbicide.

15. The method of claim 14, wherein the herbicide is selected from the group consisting of aclonifen, diuron, hexoconazole, quinchlorac, sulfentrazone, hexazinone, 2,4-D, napropamide, and combinations thereof.

* * * * *